United States Patent
Brown et al.

(10) Patent No.: US 9,645,465 B2
(45) Date of Patent: May 9, 2017

(54) CONTROLLING TRANSITIONS IN OPTICALLY SWITCHABLE DEVICES

(71) Applicant: View Inc., Milpitas, CA (US)

(72) Inventors: Stephen C. Brown, San Mateo, CA (US); Dhairya Shrivastava, Los Altos, CA (US); Anshu A. Pradhan, Collierville, TN (US); Deepika Khowal, Milpitas, CA (US); Namrata Vora, San Jose, CA (US)

(73) Assignee: View, Inc., Milpitas, CA (US)

( * ) Notice: Subject to any disclaimer, the term of this patent is extended or adjusted under 35 U.S.C. 154(b) by 0 days.

(21) Appl. No.: 14/931,390

(22) Filed: Nov. 3, 2015

(65) Prior Publication Data
US 2016/0054633 A1  Feb. 25, 2016

Related U.S. Application Data

(63) Continuation-in-part of application No. 14/163,026, filed on Jan. 24, 2014, now Pat. No. 9,423,664, which
(Continued)

(51) Int. Cl.
*G02F 1/153* (2006.01)
*G02F 1/15* (2006.01)
(Continued)

(52) U.S. Cl.
CPC ............ *G02F 1/163* (2013.01); *E06B 3/6722* (2013.01); *E06B 9/24* (2013.01); *G01J 1/0238* (2013.01);
(Continued)

(58) Field of Classification Search
CPC ..... G02F 1/1523; G02B 13/0045; G02B 9/62; G02B 13/04; G05D 23/1927;
(Continued)

(56) References Cited

U.S. PATENT DOCUMENTS

| 5,124,833 A | 6/1992 | Barton et al. |
| 5,170,108 A | 12/1992 | Peterson et al. |

(Continued)

FOREIGN PATENT DOCUMENTS

| CN | 2590732 Y | 12/2003 |
| CN | 1534413 A | 10/2004 |

(Continued)

OTHER PUBLICATIONS

US Patent Application entitled Controlling Transitions in Optically Switchable Devices filed Jan. 12, 2016 for U.S. Appl. No. 14/993,822.

(Continued)

*Primary Examiner* — William Choi
(74) *Attorney, Agent, or Firm* — Weaver Austin Villeneuve & Sampson LLP; Brian D. Griedel

(57) ABSTRACT

This disclosure provides systems, methods, and apparatus for controlling transitions in an optically switchable device. In one aspect, a controller for a tintable window may include a processor, an input for receiving output signals from sensors, and instructions for causing the processor to determine a level of tint of the tintable window, and an output for controlling the level of tint in the tintable window. The instructions may include a relationship between the received output signals and the level of tint, with the relationship employing output signals from an exterior photosensor, an interior photosensor, an occupancy sensor, an exterior temperature sensor, and a transmissivity sensor. In some instances, the controller may receive output signals over a network and/or be interfaced with a network, and in some instances, the controller may be a standalone controller that is not interfaced with a network.

10 Claims, 14 Drawing Sheets

Related U.S. Application Data is a continuation of application No. 13/449,235, filed on Apr. 17, 2012, now Pat. No. 8,705,162, application No. 14/931,390, which is a continuation-in-part of application No. 13/049,756, filed on Mar. 16, 2011, now Pat. No. 9,454,055, and a continuation-in-part of application No. 14/489,414, filed on Sep. 17, 2014, which is a continuation-in-part of application No. 13/309,990, filed on Dec. 2, 2011, now Pat. No. 8,864,321, which is a continuation of application No. 13/049,623, filed on Mar. 16, 2011, now Pat. No. 8,254,013.

(51) Int. Cl.

| | | |
|---|---|---|
| *G05D 23/00* | (2006.01) | |
| *G02F 1/163* | (2006.01) | |
| *E06B 3/67* | (2006.01) | |
| *G01J 1/02* | (2006.01) | |
| *E06B 9/24* | (2006.01) | |
| *G01K 13/00* | (2006.01) | |
| *G01J 1/42* | (2006.01) | |
| *G02F 1/133* | (2006.01) | |
| *G01N 21/59* | (2006.01) | |

(52) U.S. Cl.
CPC ........... *G01J 1/4204* (2013.01); *G01J 1/4228* (2013.01); *G01K 13/00* (2013.01); *E06B 2009/2464* (2013.01); *G01J 2001/4266* (2013.01); *G01N 21/59* (2013.01); *G02F 1/13318* (2013.01); *G02F 1/153* (2013.01)

(58) Field of Classification Search
CPC .............. G05D 23/1928; G05D 23/193; G05D 23/1931; G05D 23/1932; G05D 23/1934; G06F 1/206
USPC ......... 359/245, 265, 275, 290; 700/299, 300
See application file for complete search history.

(56) References Cited

U.S. PATENT DOCUMENTS

| | | |
|---|---|---|
| 5,204,778 A | 4/1993 | Bechtel |
| 5,220,317 A | 6/1993 | Lynam et al. |
| 5,290,986 A | 3/1994 | Colon et al. |
| 5,353,148 A | 10/1994 | Eid et al. |
| 5,365,365 A | 11/1994 | Ripoche et al. |
| 5,379,146 A | 1/1995 | Defendini |
| 5,384,578 A | 1/1995 | Lynam et al. |
| 5,402,144 A | 3/1995 | Ripoche |
| 5,451,822 A | 9/1995 | Bechtel et al. |
| 5,598,000 A | 1/1997 | Popat |
| 5,621,526 A | 4/1997 | Kuze |
| 5,673,028 A | 9/1997 | Levy |
| 5,694,144 A | 12/1997 | Lefrou et al. |
| 5,764,402 A | 6/1998 | Thomas et al. |
| 5,822,107 A | 10/1998 | Lefrou et al. |
| 5,900,720 A | 5/1999 | Kallman et al. |
| 5,956,012 A | 9/1999 | Turnbull et al. |
| 5,973,818 A | 10/1999 | Sjursen et al. |
| 5,973,819 A | 10/1999 | Pletcher et al. |
| 5,978,126 A | 11/1999 | Sjursen et al. |
| 6,039,390 A | 3/2000 | Agrawal et al. |
| 6,039,850 A | 3/2000 | Schulz et al. |
| 6,055,089 A | 4/2000 | Schulz et al. |
| 6,064,949 A | 5/2000 | Werner et al. |
| 6,084,231 A | 7/2000 | Popat |
| 6,084,700 A | 7/2000 | Knapp et al. |
| 6,130,448 A | 10/2000 | Bauer et al. |
| 6,130,772 A | 10/2000 | Cava |
| 6,222,177 B1 | 4/2001 | Bechtel et al. |
| 6,262,831 B1 | 7/2001 | Bauer et al. |
| 6,386,713 B1 | 5/2002 | Turnbull et al. |
| 6,407,468 B1 | 6/2002 | LeVesque et al. |
| 6,407,847 B1 | 6/2002 | Poll et al. |
| 6,449,082 B1 | 9/2002 | Agrawal et al. |
| 6,471,360 B2 | 10/2002 | Rukavina et al. |
| 6,535,126 B2 | 3/2003 | Lin et al. |
| 6,567,708 B1 | 5/2003 | Bechtel et al. |
| 6,614,577 B1 | 9/2003 | Yu et al. |
| 6,795,226 B2 | 9/2004 | Agrawal et al. |
| 6,829,511 B2 | 12/2004 | Bechtel et al. |
| 6,856,444 B2 | 2/2005 | Ingalls et al. |
| 6,897,936 B1 | 5/2005 | Li et al. |
| 6,940,627 B2 | 9/2005 | Freeman et al. |
| 7,085,609 B2 | 8/2006 | Bechtel et al. |
| 7,133,181 B2 | 11/2006 | Greer |
| 7,215,318 B2 | 5/2007 | Turnbull et al. |
| 7,277,215 B2 | 10/2007 | Greer |
| 7,304,787 B2 | 12/2007 | Whitesides et al. |
| 7,417,397 B2 | 8/2008 | Berman et al. |
| 7,542,809 B2 | 6/2009 | Bechtel et al. |
| 7,548,833 B2 | 6/2009 | Ahmed |
| 7,567,183 B2 | 7/2009 | Schwenke |
| 7,610,910 B2 | 11/2009 | Ahmed |
| 7,817,326 B1 | 10/2010 | Rennig et al. |
| 7,822,490 B2 | 10/2010 | Bechtel et al. |
| 7,873,490 B2 | 1/2011 | MacDonald |
| 7,941,245 B1 | 5/2011 | Popat |
| 7,972,021 B2 | 7/2011 | Scherer |
| 7,977,904 B2 | 7/2011 | Berman et al. |
| 7,990,603 B2 | 8/2011 | Ash et al. |
| 8,004,739 B2 | 8/2011 | Letocart |
| 8,018,644 B2 | 9/2011 | Gustavsson et al. |
| 8,102,586 B2 | 1/2012 | Albahri |
| 8,120,292 B2 | 2/2012 | Berman et al. |
| 8,125,172 B2 | 2/2012 | Berman et al. |
| 8,213,074 B1 | 7/2012 | Shrivastava et al. |
| 8,248,014 B2 | 8/2012 | Berman et al. |
| 8,254,013 B2 | 8/2012 | Mehtani et al. |
| 8,292,228 B2 | 10/2012 | Mitchell et al. |
| 8,456,729 B2 | 6/2013 | Brown et al. |
| 8,547,624 B2 | 10/2013 | Ash et al. |
| 8,705,162 B2 | 4/2014 | Brown et al. |
| 8,723,467 B2 | 5/2014 | Berman et al. |
| 8,836,263 B2 | 9/2014 | Berman et al. |
| 8,864,321 B2 | 10/2014 | Mehtani et al. |
| 8,902,486 B1 | 12/2014 | Chandrasekhar |
| 8,976,440 B2 | 3/2015 | Berland et al. |
| 9,016,630 B2 | 4/2015 | Mitchell et al. |
| 9,030,725 B2 | 5/2015 | Pradhan et al. |
| 9,078,299 B2 | 7/2015 | Ashdown |
| 9,081,247 B1 | 7/2015 | Pradhan et al. |
| 9,226,366 B2 | 12/2015 | Orillard et al. |
| 9,298,203 B2 | 3/2016 | Wenzel |
| 9,348,192 B2 | 5/2016 | Brown et al. |
| 9,423,664 B2 | 8/2016 | Brown et al. |
| 9,454,055 B2 | 9/2016 | Brown et al. |
| 9,546,515 B2 | 1/2017 | Hall et al. |
| 2002/0075472 A1 | 6/2002 | Holton |
| 2002/0135881 A1 | 9/2002 | Rukavina et al. |
| 2002/0152298 A1 | 10/2002 | Kikta et al. |
| 2003/0191546 A1 | 10/2003 | Bechtel et al. |
| 2003/0210449 A1 | 11/2003 | Ingalls et al. |
| 2003/0210450 A1 | 11/2003 | Yu et al. |
| 2003/0227663 A1 | 12/2003 | Agrawal et al. |
| 2003/0227664 A1 | 12/2003 | Agrawal et al. |
| 2004/0001056 A1 | 1/2004 | Atherton et al. |
| 2004/0135989 A1 | 7/2004 | Klebe |
| 2004/0160322 A1 | 8/2004 | Stilp |
| 2005/0046920 A1 | 3/2005 | Freeman et al. |
| 2005/0200934 A1 | 9/2005 | Callahan et al. |
| 2005/0225830 A1 | 10/2005 | Huang et al. |
| 2005/0268629 A1 | 12/2005 | Ahmed |
| 2005/0270620 A1 | 12/2005 | Bauer et al. |
| 2005/0278047 A1 | 12/2005 | Ahmed |
| 2006/0018000 A1 | 1/2006 | Greer |
| 2006/0107616 A1 | 5/2006 | Ratti et al. |
| 2006/0170376 A1 | 8/2006 | Piepgras et al. |
| 2006/0187608 A1 | 8/2006 | Stark |
| 2006/0209007 A1 | 9/2006 | Pyo et al. |
| 2006/0245024 A1 | 11/2006 | Greer |

(56) References Cited

U.S. PATENT DOCUMENTS

| | | |
|---|---|---|
| 2007/0002007 A1 | 1/2007 | Tam |
| 2007/0067048 A1* | 3/2007 | Bechtel .................. E06B 9/24 700/19 |
| 2007/0162233 A1 | 7/2007 | Schwenke |
| 2007/0285759 A1 | 12/2007 | Ash et al. |
| 2008/0018979 A1 | 1/2008 | Mahe et al. |
| 2009/0020233 A1 | 1/2009 | Berman et al. |
| 2009/0027759 A1 | 1/2009 | Albahri |
| 2009/0066157 A1 | 3/2009 | Tarng et al. |
| 2009/0143141 A1 | 6/2009 | Wells et al. |
| 2009/0204269 A1 | 8/2009 | Bechtel et al. |
| 2009/0243732 A1 | 10/2009 | Tarng et al. |
| 2009/0243802 A1 | 10/2009 | Wolf et al. |
| 2009/0254222 A1 | 10/2009 | Berman et al. |
| 2009/0296188 A1 | 12/2009 | Jain et al. |
| 2010/0039410 A1 | 2/2010 | Becker et al. |
| 2010/0066484 A1 | 3/2010 | Hanwright et al. |
| 2010/0082081 A1 | 4/2010 | Niessen et al. |
| 2010/0172009 A1 | 7/2010 | Matthews |
| 2010/0172010 A1 | 7/2010 | Gustavsson et al. |
| 2010/0188057 A1 | 7/2010 | Tarng |
| 2010/0235206 A1 | 9/2010 | Miller et al. |
| 2010/0243427 A1 | 9/2010 | Kozlowski et al. |
| 2010/0245972 A1 | 9/2010 | Wright |
| 2010/0315693 A1 | 12/2010 | Lam et al. |
| 2011/0046810 A1 | 2/2011 | Bechtel et al. |
| 2011/0063708 A1 | 3/2011 | Letocart |
| 2011/0148218 A1 | 6/2011 | Rozbicki |
| 2011/0164304 A1 | 7/2011 | Brown et al. |
| 2011/0167617 A1 | 7/2011 | Letocart |
| 2011/0235152 A1 | 9/2011 | Letocart |
| 2011/0249313 A1 | 10/2011 | Letocart |
| 2011/0255142 A1 | 10/2011 | Ash et al. |
| 2011/0266419 A1 | 11/2011 | Jones et al. |
| 2011/0292488 A1 | 12/2011 | McCarthy et al. |
| 2011/0304898 A1 | 12/2011 | Letocart |
| 2011/0304899 A1 | 12/2011 | Kwak et al. |
| 2012/0026573 A1 | 2/2012 | Collins et al. |
| 2012/0062975 A1 | 3/2012 | Mehtani et al. |
| 2012/0095601 A1 | 4/2012 | Abraham et al. |
| 2012/0133315 A1 | 5/2012 | Berman et al. |
| 2012/0188627 A1 | 7/2012 | Chen et al. |
| 2012/0190386 A1 | 7/2012 | Anderson |
| 2012/0194895 A1 | 8/2012 | Podbelski et al. |
| 2012/0200908 A1 | 8/2012 | Bergh et al. |
| 2012/0236386 A1 | 9/2012 | Mehtani et al. |
| 2012/0239209 A1 | 9/2012 | Brown et al. |
| 2012/0268803 A1 | 10/2012 | Greer |
| 2012/0285630 A1 | 11/2012 | Berman et al. |
| 2012/0293855 A1 | 11/2012 | Shrivastava et al. |
| 2013/0021659 A1 | 1/2013 | Friedman et al. |
| 2013/0057937 A1 | 3/2013 | Berman et al. |
| 2013/0158790 A1 | 6/2013 | McIntyre, Jr. et al. |
| 2013/0242370 A1 | 9/2013 | Wang |
| 2013/0263510 A1 | 10/2013 | Gassion |
| 2013/0271812 A1 | 10/2013 | Brown et al. |
| 2013/0271813 A1 | 10/2013 | Brown |
| 2013/0271814 A1 | 10/2013 | Brown |
| 2013/0271815 A1 | 10/2013 | Pradhan et al. |
| 2014/0067733 A1 | 3/2014 | Humann |
| 2014/0104667 A1 | 4/2014 | Greer et al. |
| 2014/0160550 A1 | 6/2014 | Brown et al. |
| 2014/0177028 A1 | 6/2014 | Shrivastava et al. |
| 2014/0236323 A1 | 8/2014 | Brown et al. |
| 2014/0259931 A1 | 9/2014 | Plummer |
| 2014/0262057 A1 | 9/2014 | Chambers et al. |
| 2014/0268287 A1 | 9/2014 | Brown et al. |
| 2014/0300945 A1 | 10/2014 | Parker |
| 2014/0303788 A1 | 10/2014 | Sanders et al. |
| 2014/0330538 A1 | 11/2014 | Conklin et al. |
| 2014/0371931 A1 | 12/2014 | Lin et al. |
| 2015/0002919 A1 | 1/2015 | Jack et al. |
| 2015/0049378 A1 | 2/2015 | Shrivastava et al. |
| 2015/0060648 A1 | 3/2015 | Brown et al. |
| 2015/0070745 A1 | 3/2015 | Pradhan |
| 2015/0116811 A1 | 4/2015 | Shrivastava et al. |
| 2015/0122474 A1 | 5/2015 | Peterson |
| 2015/0185581 A1 | 7/2015 | Pradhan et al. |
| 2015/0293422 A1 | 10/2015 | Pradhan et al. |
| 2015/0368967 A1 | 12/2015 | Lundy et al. |
| 2016/0054633 A1 | 2/2016 | Brown et al. |
| 2016/0054634 A1 | 2/2016 | Brown et al. |
| 2016/0124283 A1 | 5/2016 | Brown et al. |
| 2016/0203403 A1 | 7/2016 | Nagel et al. |
| 2017/0053068 A1 | 2/2017 | Pillai et al. |
| 2017/0075183 A1 | 3/2017 | Brown |

FOREIGN PATENT DOCUMENTS

| | | |
|---|---|---|
| CN | 1704556 A | 12/2005 |
| CN | 101707892 | 5/2010 |
| CN | 101707892 A | 5/2010 |
| CN | 101762920 A | 6/2010 |
| CN | 101969207 A | 2/2011 |
| CN | 102203370 A | 9/2011 |
| CN | 102330530 A | 1/2012 |
| DE | 10124673 A1 | 11/2002 |
| DE | 102014220818 A1 | 4/2016 |
| EP | 0445314 | 9/1991 |
| EP | 0869032 | 10/1998 |
| EP | 1078818 A2 | 2/2001 |
| EP | 1441269 | 7/2004 |
| EP | 0835475 B1 | 9/2004 |
| EP | 1510854 A1 | 3/2005 |
| EP | 1417535 | 11/2005 |
| EP | 1619546 A2 | 1/2006 |
| EP | 0920210 | 6/2009 |
| EP | 2161615 | 3/2010 |
| EP | 2357544 | 8/2011 |
| EP | 2764998 A1 | 8/2014 |
| GB | 2462754 A | 5/2004 |
| JP | 63-208830 | 8/1988 |
| JP | 02-132420 | 5/1990 |
| JP | 05-178645 | 7/1993 |
| JP | 10-063216 | 3/1998 |
| JP | 2004-245985 | 9/2004 |
| JP | 4694816 B2 | 6/2011 |
| JP | 4799113 B2 | 10/2011 |
| JP | 2013-057975 A | 3/2013 |
| KR | 20-0412640 | 3/2006 |
| KR | 10-752041 B1 | 8/2007 |
| KR | 10-2008-0022319 | 3/2008 |
| KR | 10-2009-0026181 | 3/2009 |
| KR | 10-0904847 B1 | 6/2009 |
| KR | 10-0931183 | 12/2009 |
| KR | 10-2010-0034361 | 4/2010 |
| KR | 10-2011-0003698 | 1/2011 |
| KR | 10-2011-0094672 | 8/2011 |
| TW | 200532346 A | 10/2005 |
| TW | 200920987 A | 5/2009 |
| TW | 201029838 A | 8/2010 |
| WO | WO96/32560 A1 | 10/1996 |
| WO | WO9632560 A1 | 10/1996 |
| WO | WO98/16870 | 4/1998 |
| WO | WO02/13052 | 2/2002 |
| WO | WO2004/003649 | 1/2004 |
| WO | WO2005/098811 | 10/2005 |
| WO | WO2005/103807 | 11/2005 |
| WO | WO2007/016546 A2 | 2/2007 |
| WO | WO2007/146862 | 12/2007 |
| WO | WO2008/030018 | 3/2008 |
| WO | WO2008/147322 | 12/2008 |
| WO | WO2009/124647 | 10/2009 |
| WO | WO2010/120771 | 10/2010 |
| WO | WO2011/020478 | 2/2011 |
| WO | WO2011/087684 | 7/2011 |
| WO | WO2011/087687 | 7/2011 |
| WO | WO2011/124720 | 10/2011 |
| WO | WO2011/127015 | 10/2011 |
| WO | WO2012/079159 | 6/2012 |
| WO | WO2012/080618 | 6/2012 |
| WO | WO2012/080656 | 6/2012 |
| WO | WO2012/080657 | 6/2012 |
| WO | WO2012/125332 A2 | 9/2012 |

(56) References Cited

FOREIGN PATENT DOCUMENTS

| WO | WO2012/145155 | 10/2012 |
|---|---|---|
| WO | WO2013/059674 | 4/2013 |
| WO | WO2013/102932 A2 | 7/2013 |
| WO | WO2013/109881 | 7/2013 |
| WO | WO2013/130781 A1 | 9/2013 |
| WO | WO2013/155467 | 10/2013 |
| WO | WO2014/121863 | 8/2014 |
| WO | WO2014/130471 | 8/2014 |
| WO | WO2014/134451 | 9/2014 |
| WO | WO2014/209812 A1 | 12/2014 |
| WO | WO2015/077097 A1 | 5/2015 |
| WO | WO2015/171886 | 11/2015 |
| WO | WO2016/029156 A1 | 2/2016 |
| WO | WO2016/029165 A2 | 2/2016 |
| WO | WO2016/058695 A1 | 4/2016 |
| WO | WO 2017/007942 | 1/2017 |

OTHER PUBLICATIONS

Preliminary Amendment filed Jan. 13, 2016 for U.S. Appl. No. 14/993,822.
Preliminary Amendment filed Dec. 22, 2015 for U.S. Appl. No. 13/772,969.
US Patent Application entitled Control Method for Tintable Windows filed Nov. 9, 2016.
U.S. Notice of Allowance dated Jan. 8, 2016 in U.S. Appl. No. 13/049,756.
U.S. Notice of Allowance dated Jun. 22, 2016 in U.S. Appl. No. 13/049,756.
US Office Action dated Nov. 27, 2015 in U.S. Appl. No. 14/163,026.
US Office Action dated Apr. 14, 2016 in U.S. Appl. No. 14/163,026.
Notice of Allowance dated Jun. 8, 2016 in U.S. Appl. No. 14/163,026.
Notice of Allowability (corrected) dated Jul. 28, 2016 in U.S. Appl. No. 14/163,026.
US Office Action dated Nov. 19, 2015 in U.S. Appl. No. 14/535,080.
US Office Action dated Feb. 22, 2016 in U.S. Appl. No. 14/535,080.
Notice of Allowance dated Apr. 4, 2016 in U.S. Appl. No. 14/535,080.
US Office Action dated Jan. 5, 2016 in U.S. Appl. No. 13/772,969.
US Final Office Action dated Jul. 29, 2016 in U.S. Appl. No. 13/772,969 .
Australian Examination Report dated Sep. 9, 2016 in AU Application No. 2013249621.
Chinese Office Action dated Apr. 5, 2016 in Chinese Application No. 201280023631.4.
Chinese Office Action dated Jun. 27, 2016 in Chinese Application No. 201480022064.X.
EPO Communication dated Sep. 2, 2015 in European Application No. 14753897.9 re Third-Party Observations.
European Search Report dated May 11, 2016 in European Application No. 13777540.9.
EP Invitation to Indicate Search dated Jun. 22, 2016 in EP Application No. 14753897.9.
European Extended Search Report dated Oct. 12, 2016 in EP Application No. 14753897.9.
International Search Report and Written Opinion dated Jul. 23, 2015 in PCT/US2015/029675.
International Preliminary Report on Patentability dated Nov. 24, 2016 in PCT/US2015/029675.
International Search Report and Written Opinion dated Dec. 13, 2016, issued in PCT/US16/55005.
International Search Report and Written Opinion dated Oct. 13, 2016, issued in PCT/US2016/041344.
Taiwanese Office Action dated Jan. 11, 2016 in TW Application No. 101108958.
Taiwanese Office Action dated Nov. 23, 2016 in TW Application No. 105129854.

Benson D. K. et al., "Design goals and challenges for a photovoltaic-powered electrochromic window covering", Solar Energy Materials and Solar Cells, vol. 39, No. 2/04, Dec. 1995, pp. 203-211.
American Chemical Society, "Solar smart window could offer privacy and light control on demand (video)," EurakAlert! Pub Release, Nov. 16, 2016 [https://www.eurekalert.org/pub_releases/2016-11/acs-ssw111616.php].
U.S. Appl. No. 14/468,778, filed Aug. 26, 2014.
U.S. Appl. No. 14/489,414, filed Sep. 17, 2014.
U.S. Appl. No. 14/535,080, filed Nov. 6, 2014 + preliminary amendment filed Nov. 7, 2014.
Preliminary Amendment filed Oct. 7, 2014 for U.S. Appl. No. 14/391,122.
U.S. Appl. No. 14/657,380, filed Mar. 13, 2015 + preliminary amendment filed Mar. 16, 2015.
U.S. Appl. No. 14/735,043, filed Jun. 9, 2015 and Preliminary Amendment filed Jul. 2, 2015.
U.S. Office Action dated Jan. 18, 2013 in U.S. Appl. No. 13/049,756.
U.S. Final Office Action dated Aug. 19, 2013 in U.S. Appl. No. 13/049,756.
U.S. Office Action dated Oct. 6, 2014 in U.S. Appl. No. 13/049,756.
U.S. Final Office Action dated Jul. 2, 2015 in U.S. Appl. No. 13/049,756.
U.S. Office Action dated Oct. 6, 2014 in U.S. Appl. No. 13/968,258.
U.S. Final Office Action dated Jun. 5, 2015 U.S. Appl. No. 13/968,258.
US Office Action dated Feb. 3, 2012 in U.S. Appl. No. 13/049,750.
US Final Office Action dated Apr. 30, 2012 in U.S. Appl. No. 13/049,750.
US Notice of Allowance dated May 8, 2012 in U.S. Appl. No. 13/049,750.
US Office Action dated Sep. 23, 2013 in U.S. Appl. No. 13/479,137.
US Final Office Action dated Jan. 27, 2014 in U.S. Appl. No. 13/479,137.
US Office Action dated Jul. 3, 2014 in U.S. Appl. No. 13/479,137.
US Final Office Action dated Feb. 26, 2015 in U.S. Appl. No. 13/479,137.
US Notice of Allowance dated May 14, 2015 in U.S. Appl. No. 13/479,137.
US Notice of Allowance (supplemental) dated Jun. 12, 2015 in U.S. Appl. No. 13/479,137.
US Office Action dated Jan. 16, 2015 in U.S. Appl. No. 14/468,778.
US Office Action dated Mar. 27, 2012 in U.S. Appl. No. 13/049,623.
US Notice of Allowance dated Jul. 20, 2012 in U.S. Appl. No. 13/049,623.
US Office Action dated Dec. 24, 2013 in U.S. Appl. No. 13/309,990.
Notice of Allowanced dated Jun. 17, 2014 in U.S. Appl. No. 13/309,990.
US Office Action dated Oct. 11, 2013 in U.S. Appl. No. 13/449,235.
US Notice of Allowance dated Jan. 10, 2014 in U.S. Appl. No. 13/449,235.
US Office Action dated Feb. 24, 2015 in U.S. Appl. No. 14/163,026.
US Office Action dated Nov. 29, 2013 in U.S. Appl. No. 13/449,248.
US Office Action dated Nov. 29, 2013 in U.S. Appl. No. 13/449,251.
US Final Office Action dated May 16, 2014 in U.S. Appl. No. 13/449,248.
US Office Action dated Sep. 29, 2014 in U.S. Appl. No. 13/449,248.
US Final Office Action dated May 15, 2014 in U.S. Appl. No. 13/449,251.
US Office Action dated Oct. 28, 2014 in U.S. Appl. No. 13/449,251.
US Office Action dated Jun. 3, 2015 in U.S. Appl. No. 13/449,251.
US Office Action dated Sep. 15, 2014 in U.S. Appl. No. 13/682,618.
US Notice of Allowance dated Jan. 22, 2015 in U.S. Appl. No. 13/682,618.
US Notice of Allowance dated Apr. 13, 2015 in U.S. Appl. No. 14/657,380.
Letter dated Dec. 1, 2014 re Prior Art re U.S. Appl. No. 13/772,969 from Ryan D. Ricks representing MechoShade Systems, Inc.
Third-Party Submission dated Feb. 2, 2015 and Feb. 18, 2015 PTO Notice re Third-Party Submission for U.S. Appl. No. 13/772,969.

(56) References Cited

OTHER PUBLICATIONS

International Search Report and Written Opinion dated Sep. 26, 2012, issued in PCT/US2012/027828.
International Preliminary Report on Patentability dated Sep. 26, 2013, issued in PCT/US2012/027828.
International Search Report and Written Opinion dated Sep. 24, 2012, issued in PCT/US2012/027909.
International Preliminary Report on Patentability dated Sep. 26, 2013, issued in PCT/US2012/027909.
International Search Report and Written Opinion dated Sep. 24, 2012, issued in PCT/US2012/027742.
International Preliminary Report on Patentability dated Sep. 26, 2013, issued in PCT/US2012/027742.
International Search Report and Written Opinion dated Mar. 28, 2013 in PCT/US2012/061137.
International Preliminary Report on Patentability dated May 1, 2014 in PCT/US2012/061137.
International Search Report and Written Opinion dated Jul. 23, 2013, issued in PCT/US2013/036235.
International Preliminary Report on Patentability dated Oct. 30, 2014 issued in PCT/US2013/036235.
International Search Report and Written Opinion dated Jul. 26, 2013, issued in PCT/US2013/036456.
International Preliminary Report on Patentability dated Oct. 23, 2014 issued in PCT/US2013/036456.
International Search Report and Written Opinion dated Jul. 11, 2013, issued in PCT/US2013/034998.
International Preliminary Report on Patentability dated Oct. 30, 2014 issued in PCT/US2013/034998.
International Search Report and Written Opinion dated Dec. 26, 2013, issued in PCT/US2013/053625.
International Preliminary Report on Patentability dated Feb. 19, 2015 issued in PCT/US2013/053625.
International Search Report and Written Opinion dated May 26, 2014, issued in PCT/US2014/016974.
International Preliminary Report on Patentability dated Sep. 3, 2015, issued in PCT/US2014/016974.
Communication re Third-Party Observation dated Dec. 4, 2014 and Third-Party Observation dated Dec. 3, 2014 in PCT/US2014/016974.
International Search Report and Written Opinion dated Oct. 16, 2014, issued in PCT/US2014/043514.
Chinese Office Action dated Jun. 26, 2015 in Chinese Application No. 201280023631.4.
Chinese Office Action dated Mar. 26, 2015 in Chinese Application No. 2015032301101560.
Chinese Office Action dated Oct. 10, 2015 in Chinese Application No. 201380026428.7.
European Search Report dated Aug. 11, 2014 in European Application No. 12757877.1.
European Search Report dated Jul. 29, 2014 in European Application No. 12758250.0.
European Search Report dated Jul. 23, 2014 in European Application No. 12756917.6.
European Search Report dated Mar. 5, 2015 in European Application No. 12841714.4.
Lim, Sunnie H.N. et al., "Modeling of optical and energy performance of tungsten-oxide-based electrochromic windows including their intermediate states," Solar Energy Materials & Solar Cells, vol. 108, Oct. 16, 2012, pp. 129-135.
"SageGlass helps Solar Decathlon-and AIA award-winning home achieve net-zero energy efficiency" in MarketWatch.com, http://www.marketwatch.com/story/sageglass-helps-solar-decathlon-and-aia-award-winning-home-achieve-net-zero-energy-efficiency-2012-06-07, Jun. 7, 2012.
"New from Pella: Windows with Smartphone-run blinds", Pella Corp., http://www.desmoinesregister.com/article/20120114/BUSINESS/301140031/0/biggame/?odyssey=nav%7Chead, Jan. 13, 2012.
"How Cleantech wants to make a 2012 comeback" http://mountainview.patch.com/articles/how-cleantech-wants-to-make-a-2012-comeback, Jan. 23, 2012.
APC by Schneider Electric, Smart-UPS 120V Product Brochure, 2013, 8 pp.
Hoosier Energy, "How do they do that? Measuring Real-Time Cloud Activity" Hoosier Energy Current Connections, undated. (http://members.questline.com/Article.aspx?articleID=18550&accountID=196000&nl=11774).
Kleissl, Jan et al., "Recent Advances in Solar Variability Modeling and Solar Forecasting at UC San Diego," Proceedings, American Solar Energy Society, 2013 Solar Conference, Apr. 16-20, 2013, Baltimore, MD.
Haby, Jeff, "Cloud Detection (IR v. VIS)," (undated) [http://theweatherprediction.com/habyhints2/512/].
Graham, Steve, "Clouds & Radiation," Mar. 1, 1999. [http://earthobservatory.nasa.gov/Features/Clouds/].
National Aeronautics & Space Administration, "Cloud Radar System (CRS)," (undated) [http://har.gsfc.nasa.gov/index.php?section=12].
Science and Technology Facilities Council. "Cloud Radar: Predicting the Weather More Accurately." ScienceDaily, Oct. 1, 2008. [www.sciencedaily.com/releases/2008/09/080924085200.htm].
"Remote Sensing: Clouds," Department of Atmospheric and Ocean Science, University of Maryland, (undated) [http://www.atmos.umd.edu/~pinker/remote sensing clouds.htm].
National Aeronautics & Space Administration, "Cloud Remote Sensing and Modeling," (undated) [http://atmospheres.gsfc.nasa.gov/climate/index.php?section=134].
Kipp & Zonen, "Solar Radiation" (undated) [http://www.kippzonen.com/Knowledge-Center/Theoretical-info/Solar-Radiation].
Duchon, Claude E. et al., "Estimating Cloud Type from Pyranometer Observations," Journal of Applied Meteorology, vol. 38, Jan. 1999, pp. 132-141.
U.S. Appl. No. 15/442,509, filed Feb. 24, 2017, Brown.
US Office Action dated Mar. 8, 2017 in U.S. Appl. No. 14/993,822.
Preliminary Amendment dated Mar. 1, 2017 for U.S. Appl. No. 15/442,509.
Preliminary Amendment dated Feb. 2, 2017 for U.S. Appl. No. 15/349,860.

* cited by examiner

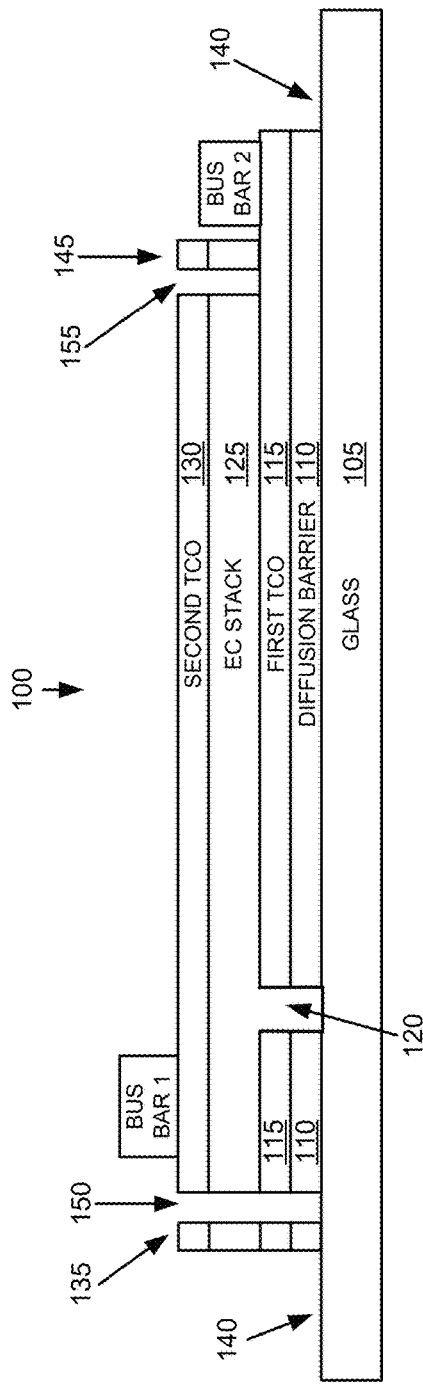
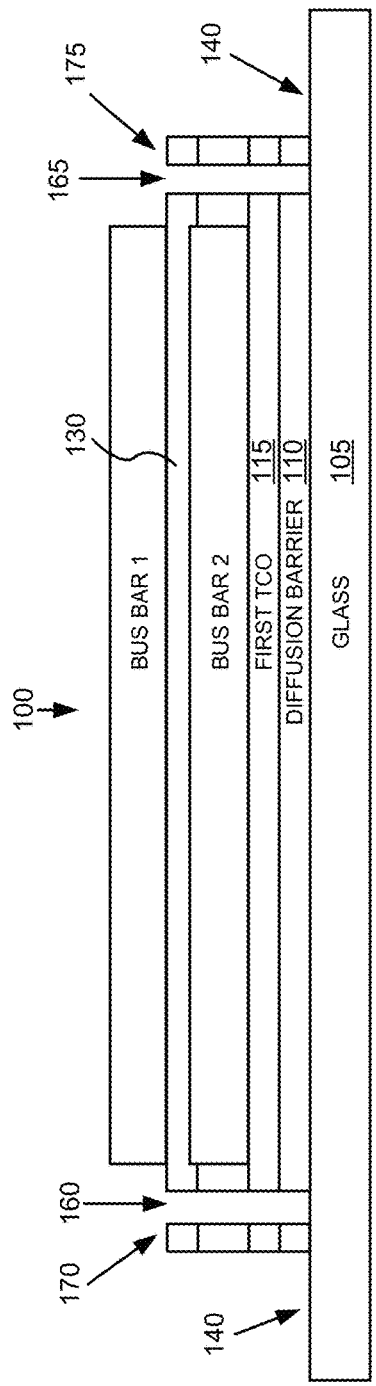

$$OV = k_1(EP) + k_2(IP) + k_3(T) + k_4(TC)$$

$k_1$ = weighting constant    OV = output value
$k_2$ = weighting constant    EP = exterior photosensor output
$k_3$ = weighting constant    IP = interior photosensor output
$k_4$ = weighting constant    T = temperature sensor output
                                      TC = tint command output

*Fig. 6*

|  | $k_1$ | $k_2$ | $k_3$ | $k_4$ |
| --- | --- | --- | --- | --- |
| schedule 1 | 0.13 | 0 | 0 | 0 |
| schedule 2 | 0.10 | 0.35 | 0.22 | 0.52 |
| schedule 3 | 0.15 | 0.35 | 0.11 | -0.52 |

*Fig. 7*

CONTROLLING TRANSITIONS IN OPTICALLY SWITCHABLE DEVICES

CROSS REFERENCE TO RELATED APPLICATIONS

This application is a continuation-in-part of U.S. patent application Ser. No. 14/163,026, filed on Jan. 24, 2014 and titled "CONTROLLING TRANSITIONS IN OPTICALLY SWITCHABLE DEVICES," which is a continuation of U.S. patent application Ser. No. 13/449,235 (now U.S. Pat. No. 8,705,162), filed on Apr. 17, 2012 and titled "CONTROLLING TRANSITIONS IN OPTICALLY SWITCHABLE DEVICES," both of which are hereby incorporated by reference in their entirety and for all purposes. This application is also a continuation-in-part of U.S. patent application Ser. No. 13/049,756, filed on Mar. 16, 2011 and titled "MULTIPURPOSE CONTROLLER FOR MULTISTATE WINDOWS," which is hereby incorporated by reference in its entirety and for all purposes. This application is also a continuation-in-part of U.S. patent application Ser. No. 14/489,414, filed on Sep. 17, 2014 and titled "CONTROLLING TRANSITIONS IN OPTICALLY SWITCHABLE DEVICES," which is a continuation-in-part of U.S. patent application Ser. No. 13/309,990, filed on Dec. 2, 2011 and titled "CONTROLLING TRANSITIONS IN OPTICALLY SWITCHABLE DEVICES," which is a continuation of U.S. patent application Ser. No. 13/049,623 (now U.S. Pat. No. 8,254,013), filed on Mar. 16, 2011 and titled "CONTROLLING TRANSITIONS IN OPTICALLY SWITCHABLE DEVICES;" all of which are hereby incorporated by reference in their entirety and for all purposes.

FIELD

The embodiments disclosed herein relate generally to electrochromic devices, more particularly to controllers and related algorithms for electrochromic windows.

BACKGROUND

Electrochromism is a phenomenon in which a material exhibits a reversible electrochemically-mediated change in an optical property when placed in a different electronic state, typically by being subjected to a voltage change. The optical property is typically one or more of color, transmittance, absorbance, and reflectance. One well known electrochromic material is tungsten oxide (WO3). Tungsten oxide is a cathodic electrochromic material in which a coloration transition, transparent to blue, occurs by electrochemical reduction.

Electrochromic materials may be incorporated into, for example, windows for home, commercial and other uses. The color, transmittance, absorbance, and/or reflectance of such windows may be changed by inducing a change in the electrochromic material, that is, electrochromic windows are windows that can be darkened or lightened electronically. A small voltage applied to an electrochromic device (EC) of the window will cause them to darken; reversing the voltage causes them to lighten. This capability allows control of the amount of light that passes through the windows, and presents an opportunity for electrochromic windows to be used as energy-saving devices.

While electrochromism was discovered in the 1960's, EC devices, and particularly EC windows, still unfortunately suffer various problems and have not begun to realize their full commercial potential despite many recent advancements in EC technology, apparatus and related methods of making and/or using EC devices.

SUMMARY

Systems, methods, and apparatus for controlling transitions in an optically switchable device are disclosed herein.

In one aspect, a method of limiting energy consumption in a facility having at least one tintable window between an interior and exterior of the facility is provided. The level of tinting in the tintable window can be controlled automatically. The method includes receiving output signals from any two or more sensors selected from the group consisting of an exterior photosensor, an interior photosensor, an occupancy sensor, an exterior temperature sensor, and a transmissivity sensor which detects light passing through the tintable window from the exterior. A level of tint for the tintable window is determined using a relationship between the received output signals and the level of tint. Instructions to change the tint of the tintable window to the level of tint determined are provided.

In another aspect, a controller for a tintable window for a facility having at least one tintable window between an interior and exterior of the facility is provided. The controller includes a processor or control circuit, at least one input for receiving output signals from one or more sensors, and instructions for causing the processor or control circuit to determine a level of tint in the tintable window by using a relationship between the received output signals and the level of tint. The relationship employs output signals from any two or more sensors selected from the group consisting of an exterior photosensor, an interior photosensor, an occupancy sensor, an exterior temperature sensor, and a transmissivity sensor which detects light passing through the tintable window from the exterior. The controller further includes at least one output for controlling, directly or indirectly, the level of tint in the tintable window.

In another aspect, a system for controlling energy consumption in a facility that contains a tintable window between an interior and exterior of the facility is provided. The system includes a building management system, a lighting control panel, a network over which the building management system and the lighting control panel communicate, and a controller for the tintable window. The controller includes instructions for determining a level of tint in the tintable window by using a relationship between received output signals and the level of tint. The relationship employs output signals from any two or more sensors selected from the group consisting of an exterior photosensor, an interior photosensor, an occupancy sensor, an exterior temperature sensor, and a transmissivity sensor which detects light passing through the tintable window from the exterior. The controller further includes at least one output for controlling, directly or indirectly, the level of tint in the tintable window.

In another aspect, a method of minimizing energy consumption in a facility having a tintable window between an exterior and an interior of the facility is provided. The tintable window has an adjustable level of tint controllable from a controller. The method includes receiving a signal indicating energy or power consumption by a heating system, a cooling system, and/or lighting within the facility, determining a level of tint for the tintable window using the signal indicating energy or power consumption of a device or system within the facility, and providing instructions to set the level of tint in the tintable window to the determined level of tint.

In another aspect, a controller for a tintable window for a facility having at least one tintable window between an interior and exterior of the facility is provided. The controller includes a processor or control circuit, at least one input for receiving output signals from one or more sensors, and instructions for causing the processor or control circuit to determine a level of tint in the tintable window by using a relationship between the received output signals and the level of tint. The relationship employs output signals from an exterior photosensor, an interior photosensor, an outside temperature sensor, and a tint command. The controller further includes at least one output for controlling, directly or indirectly, the level of tint in the tintable window.

In another aspect, a method of limiting energy consumption in a facility having at least one tintable window between an interior and exterior of the facility is provided. The level of tinting in the tintable window can be controlled automatically. The method includes receiving signals indicating a level of exterior irradiance received at or proximate the tintable window and determining a level of tint for the tintable window using a relationship between the received output signals and the level of tint. The relationship requires (i) transitioning from a first darker tint level to a second lighter tint level when the received level of irradiance passes a first threshold and (ii) transitioning from the second lighter tint level to the first darker tint level when the received level of irradiance passes a second threshold. The first and second thresholds are different. The method further includes providing instructions to change the tint of the tintable window to the determined level of tint.

These and other features and advantages will be described in further detail below, with reference to the associated drawings.

BRIEF DESCRIPTION OF THE DRAWINGS

The following detailed description can be more fully understood when considered in conjunction with the drawings in which:

FIGS. 1A-1C show schematic diagrams of electrochromic devices formed on glass substrates, i.e., electrochromic lites.

FIG. 6 shows a function that may be used to determine the level of tint of an electrochromic window.

FIG. 7 shows a schedule of weighting constants that may be used with the function shown in FIG. 6.

DETAILED DESCRIPTION

Window controllers described herein are used to control tintable windows, including electrochromic windows. Virtually any tintable and/or reflective window or mirror will work with the window controllers described herein. For example, non-electrochromic optically switchable devices such liquid crystal devices and suspended particle devices may be used with the described window controllers.

The window controllers described herein significantly augment environmental control in a building, for example, when the window controllers are integrated with a building management system (BMS). Interrelationships between window performance, microclimate sensing, and environmental control are described in more detail below.

Figure 5:
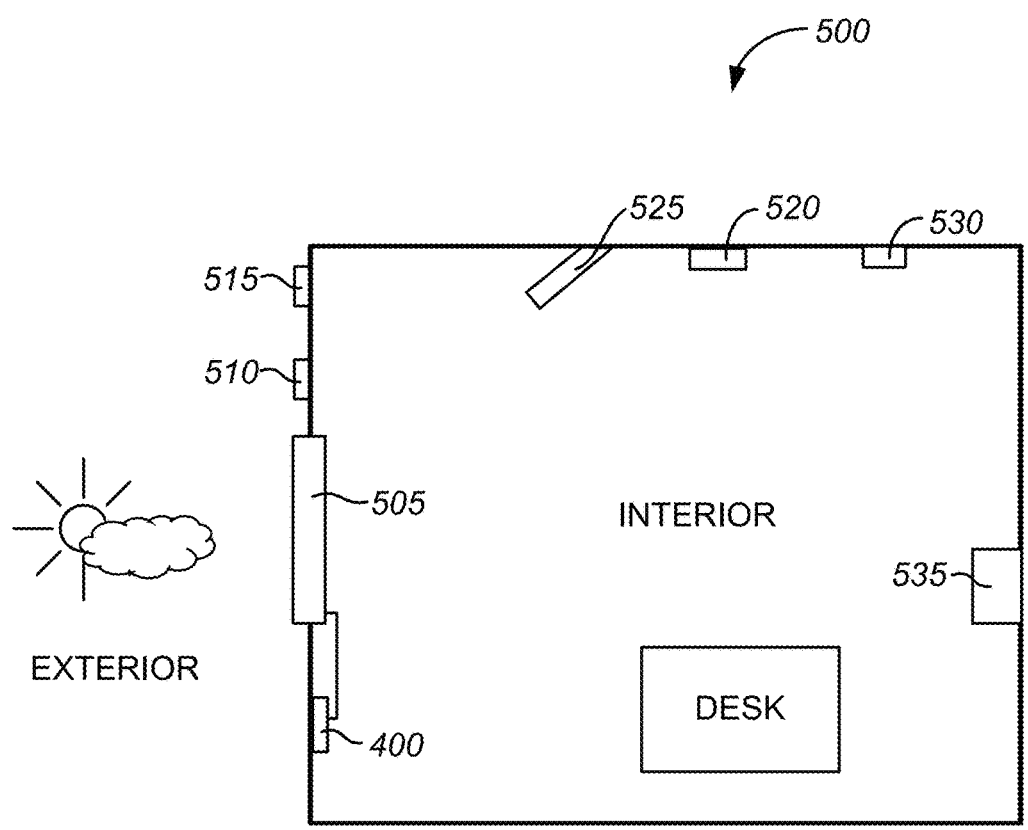
FIG. 5 depicts a schematic diagram of a room including an electrochromic window and a plurality of sensors.

For example, as shown in FIGS. 5, 6, and 7, a standalone window controller may receive input from various sensors, including an exterior photosensor, an interior photosensor, a temperature sensor, an interior transmissivity sensor, an occupancy sensor, and a power meter. These inputs may be processed by the window controller to determine a desired tint for a tintable window using, for example, a function (e.g., see FIG. 6) or a lookup table. The function or lookup table may change with the time of day or the day of the year to account for the changes in sunlight incident upon the tintable window (e.g., see FIG. 7). Further, tintable windows and a window controller may be integrated into a building including a building network or a BMS (e.g., see FIGS. 11 and 12). The window controller may interface with the different systems of the building to aid in the control of the environment in the building.

Overview of Electrochromic Devices

It should be understood that while the disclosed embodiments focus on electrochromic (EC) windows (also referred to as smart windows), the concepts disclosed herein may apply to other types of tintable windows. For example, a window incorporating a liquid crystal device or a suspended particle device, instead of an electrochromic device, could be incorporated in any of the disclosed embodiments.

In order to orient the reader to the embodiments of systems, window controllers, and methods disclosed herein, a brief discussion of electrochromic devices is provided. This initial discussion of electrochromic devices is provided for context only, and the subsequently described embodiments of systems, window controllers, and methods are not limited to the specific features and fabrication processes of this initial discussion.

Figure 1C:
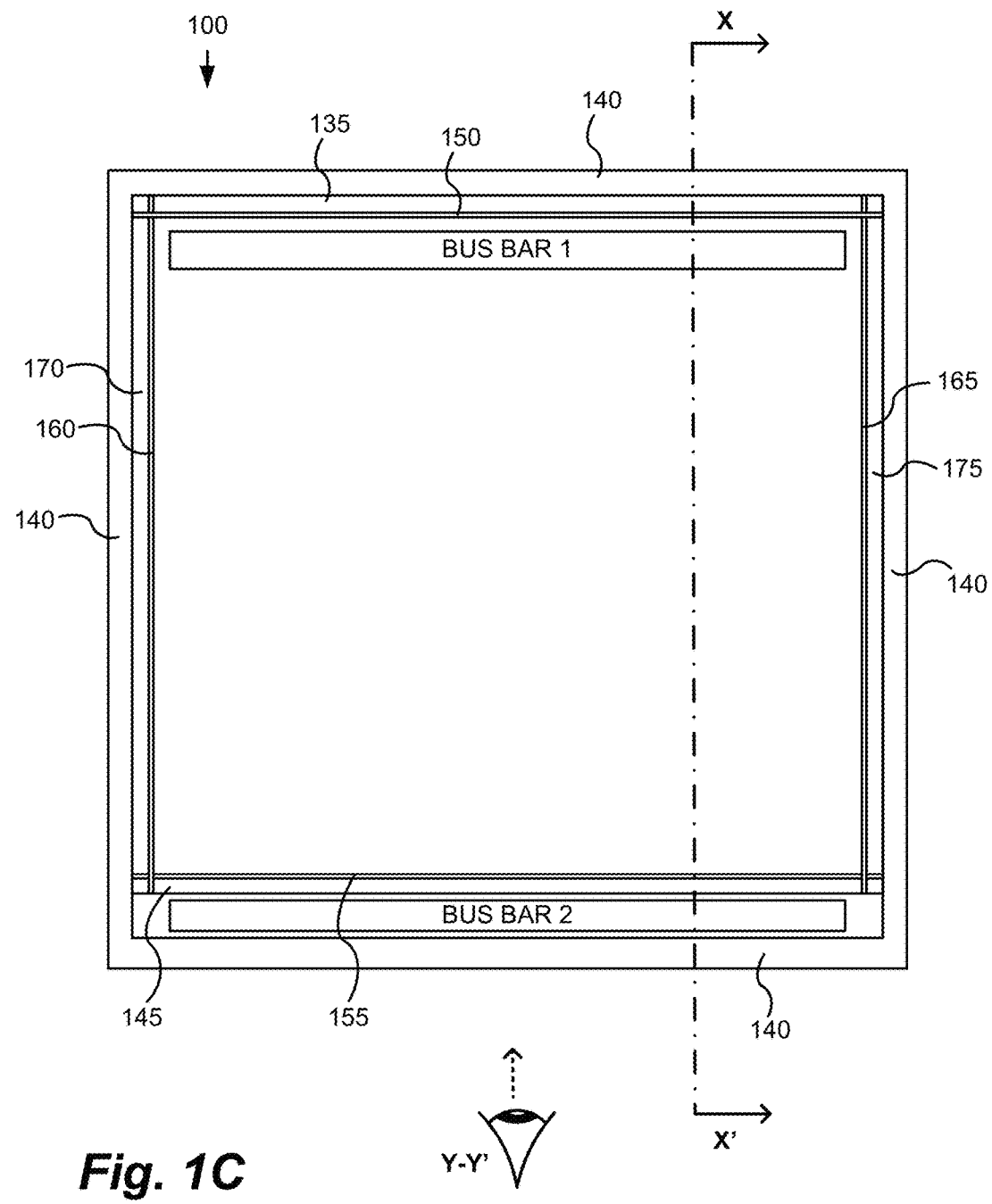

A particular example of an electrochromic lite is described with reference to FIGS. 1A-1C, in order to illustrate embodiments described herein. FIG. 1A is a cross-sectional representation (see cut X-X' of FIG. 1C) of an electrochromic lite, 100, which is fabricated starting with a glass sheet, 105. FIG. 1B shows an end view (see perspective Y-Y' of FIG. 1C) of EC lite 100, and FIG. 1C shows a top-down view of EC lite 100. FIG. 1A shows the electrochromic lite after fabrication on glass sheet 105, edge deleted to produce area, 140, around the perimeter of the lite.

The electrochromic lite has also been laser scribed and bus bars have been attached. The glass lite 105 has a diffusion barrier, 110, and a first transparent conducting oxide (TCO), 115, on the diffusion barrier. In this example, the edge deletion process removes both TCO 115 and diffusion barrier 110, but in other embodiments only the TCO is removed, leaving the diffusion barrier intact. The TCO 115 is the first of two conductive layers used to form the electrodes of the electrochromic device fabricated on the glass sheet. In this example, the glass sheet includes underlying glass and the diffusion barrier layer. Thus, in this example, the diffusion barrier is formed, and then the first TCO, an EC stack, 125, (e.g., having electrochromic, ion conductor, and counter electrode layers), and a second TCO, 130, are formed. In one embodiment, the electrochromic device (EC stack and second TCO) is fabricated in an integrated deposition system where the glass sheet does not leave the integrated deposition system at any time during fabrication of the stack. In one embodiment, the first TCO layer is also formed using the integrated deposition system where the glass sheet does not leave the integrated deposition system during deposition of the EC stack and the (second) TCO layer. In one embodiment, all of the layers (diffusion barrier, first TCO, EC stack, and second TCO) are deposited in the integrated deposition system where the glass sheet does not leave the integrated deposition system during deposition. In this example, prior to deposition of EC stack 125, an isolation trench, 120, is cut through TCO 115 and diffusion barrier 110. Trench 120 is made in contemplation of electrically isolating an area of TCO 115 that will reside under bus bar 1 after fabrication is complete (see FIG. 1A). This is done to avoid charge buildup and coloration of the EC device under the bus bar, which can be undesirable.

After formation of the EC device, edge deletion processes and additional laser scribing are performed. FIG. 1A depicts areas 140 where the device has been removed, in this example, from a perimeter region surrounding laser scribe trenches, 150, 155, 160, and 165. Trenches 150, 160 and 165 pass through the EC stack and also through the first TCO and diffusion barrier. Trench 155 passes through second TCO 130 and the EC stack, but not the first TCO 115. Laser scribe trenches 150, 155, 160, and 165 are made to isolate portions of the EC device, 135, 145, 170, and 175, which were potentially damaged during edge deletion processes from the operable EC device. In this example, laser scribe trenches 150, 160, and 165 pass through the first TCO to aid in isolation of the device (laser scribe trench 155 does not pass through the first TCO, otherwise it would cut off bus bar 2's electrical communication with the first TCO and thus the EC stack). The laser or lasers used for the laser scribe processes are typically, but not necessarily, pulse-type lasers, for example, diode-pumped solid state lasers. For example, the laser scribe processes can be performed using a suitable laser from IPG Photonics (of Oxford, Mass.), or from Ekspla (of Vilnius, Lithuania). Scribing can also be performed mechanically, for example, by a diamond tipped scribe. One of ordinary skill in the art would appreciate that the laser scribing processes can be performed at different depths and/or performed in a single process whereby the laser cutting depth is varied, or not, during a continuous path around the perimeter of the EC device. In one embodiment, the edge deletion is performed to the depth of the first TCO.

After laser scribing is complete, bus bars are attached. Non-penetrating bus bar (1) is applied to the second TCO. Non-penetrating bus bar (2) is applied to an area where the device was not deposited (e.g., from a mask protecting the first TCO from device deposition), in contact with the first TCO or, in this example, where an edge deletion process (e.g., laser ablation using an apparatus having a XY or XYZ galvanometer) was used to remove material down to the first TCO. In this example, both bus bar 1 and bus bar 2 are non-penetrating bus bars. A penetrating bus bar is one that is typically pressed into and through the EC stack to make contact with the TCO at the bottom of the stack. A non-penetrating bus bar is one that does not penetrate into the EC stack layers, but rather makes electrical and physical contact on the surface of a conductive layer, for example, a TCO.

The TCO layers can be electrically connected using a non-traditional bus bar, for example, a bus bar fabricated with screen and lithography patterning methods. In one embodiment, electrical communication is established with the device's transparent conducting layers via silk screening (or using another patterning method) a conductive ink followed by heat curing or sintering the ink. Advantages to using the above described device configuration include simpler manufacturing, for example, and less laser scribing than conventional techniques which use penetrating bus bars.

After the bus bars are connected, the device is integrated into an insulated glass unit (IGU), which includes, for example, wiring the bus bars and the like. In some embodiments, one or both of the bus bars are inside the finished IGU, however in one embodiment one bus bar is outside the seal of the IGU and one bus bar is inside the IGU. In the former embodiment, area 140 is used to make the seal with one face of the spacer used to form the IGU. Thus, the wires or other connection to the bus bars runs between the spacer and the glass. As many spacers are made of metal, e.g., stainless steel, which is conductive, it is desirable to take steps to avoid short circuiting due to electrical communication between the bus bar and connector thereto and the metal spacer.

Figure 2A:
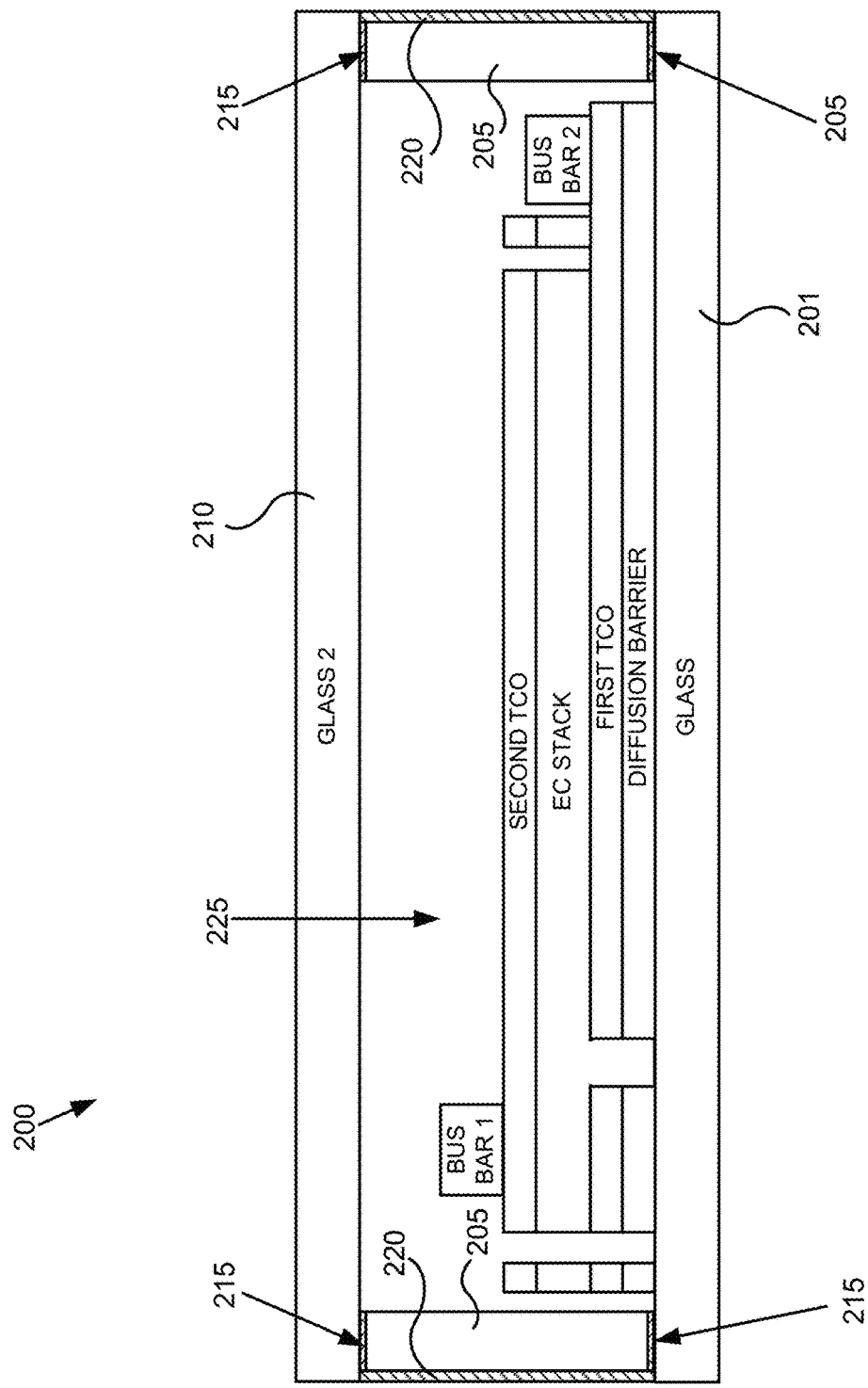
FIGS. 2A and 2B show cross-sectional schematic diagrams of the electrochromic lites as described in relation to FIGS. 1A-C integrated into an IGU.
Figure 2B:
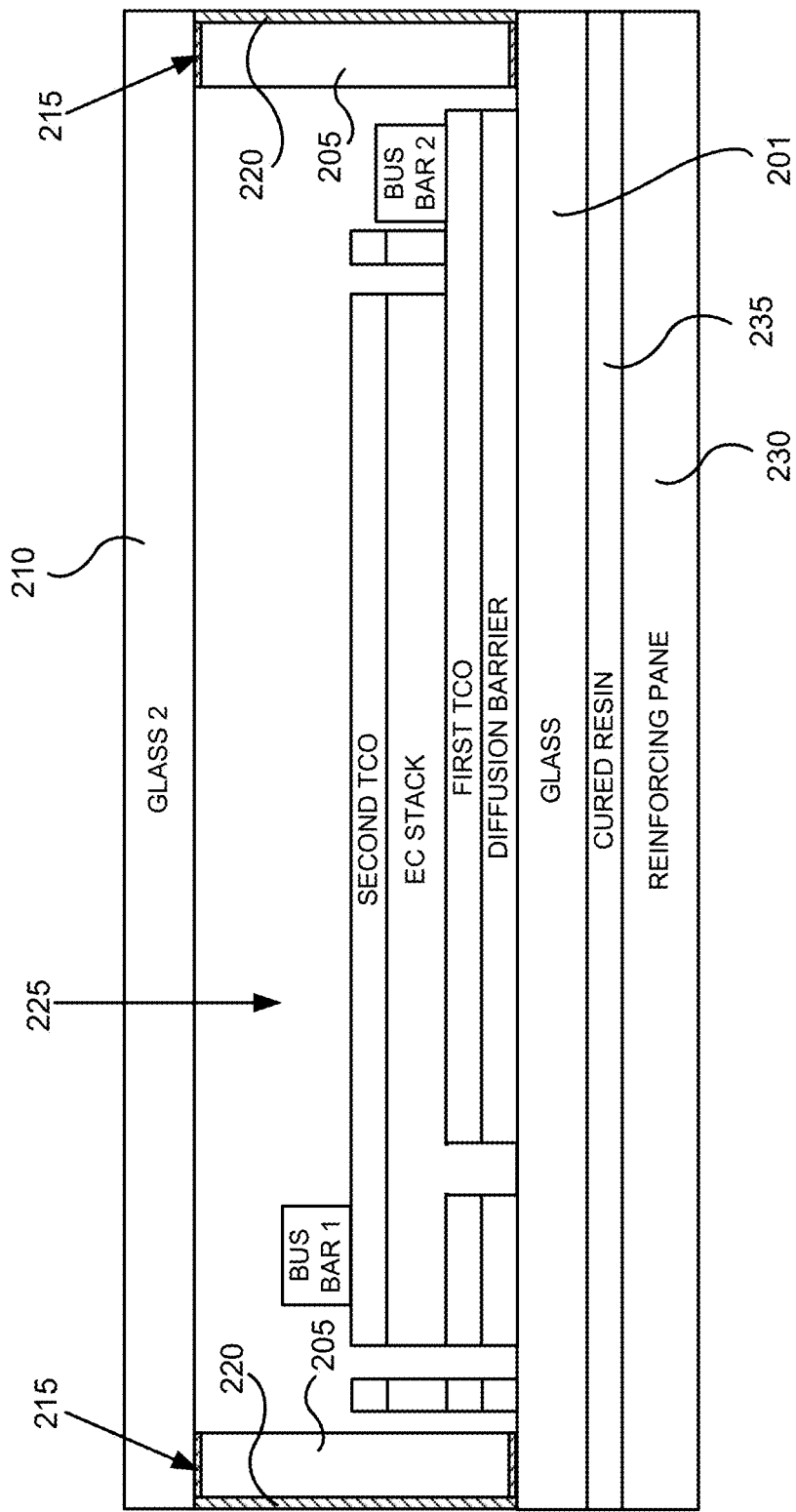

As described above, after the bus bars are connected, the electrochromic lite is integrated into an IGU, which includes, for example, wiring for the bus bars and the like. In the embodiments described herein, both of the bus bars are inside the primary seal of the finished IGU. FIG. 2A shows a cross-sectional schematic diagram of the electrochromic window as described in relation to FIGS. 1A-C integrated into an IGU, 200. A spacer, 205, is used to separate the electrochromic lite from a second lite, 210. Second lite 210 in IGU 200 is a non-electrochromic lite, however, the embodiments disclosed herein are not so limited. For example, lite 210 can have an electrochromic device thereon and/or one or more coatings such as low-E coatings and the like. Lite 201 can also be laminated glass, such as depicted in FIG. 2B (lite 201 is laminated to reinforcing pane, 230, via resin, 235). Between spacer 205 and the first TCO layer of the electrochromic lite is a primary seal material, 215. This primary seal material is also between spacer 205 and second glass lite 210. Around the perimeter of spacer 205 is a secondary seal, 220. Bus bar wiring/leads traverse the seals for connection to a controller. Secondary seal 220 may be much thicker that depicted. These seals aid in keeping moisture out of an interior space, 225, of the IGU. They also serve to prevent argon or other gas in the interior of the IGU from escaping.

Figure 3A:
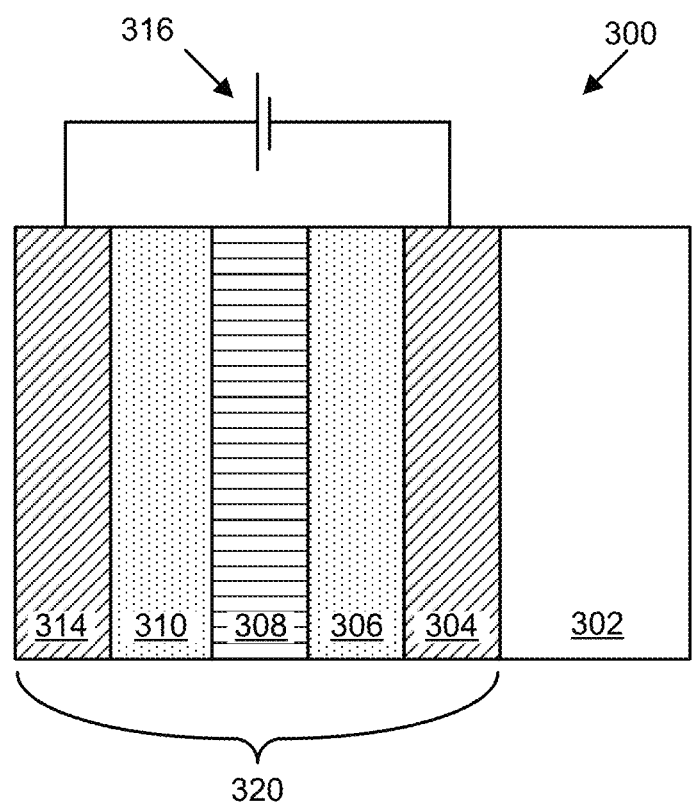
FIG. 3A depicts a schematic cross-section of an electrochromic device.

FIG. 3A schematically depicts an electrochromic device, 300, in cross-section. Electrochromic device 300 includes a substrate, 302, a first conductive layer (CL), 304, an electrochromic layer (EC), 306, an ion conducting layer (IC), 308, a counter electrode layer (CE), 310, and a second conductive layer (CL), 314. Layers 304, 306, 308, 310, and 314 are collectively referred to as an electrochromic stack

320. A voltage source 316 operable to apply an electric potential across electrochromic stack 320 effects the transition of the electrochromic device from, for example, a bleached state to a colored state (depicted). The order of layers can be reversed with respect to the substrate.

Electrochromic devices having distinct layers as described can be fabricated as all solid state devices and/or all inorganic devices having low defectivity. Such devices and methods of fabricating them are described in more detail in U.S. patent application Ser. No. 12/645,111, entitled, "Fabrication of Low-Defectivity Electrochromic Devices," filed on Dec. 22, 2009 and naming Mark Kozlowski et al. as inventors, and in U.S. patent application Ser. No. 12/645,159, entitled, "Electrochromic Devices," filed on Dec. 22, 2009 and naming Zhongchun Wang et al. as inventors, both of which are incorporated by reference herein for all purposes. It should be understood, however, that any one or more of the layers in the stack may contain some amount of organic material. The same can be said for liquids that may be present in one or more layers in small amounts. It should also be understood that solid state material may be deposited or otherwise formed by processes employing liquid components such as certain processes employing sol-gels or chemical vapor deposition.

Additionally, it should be understood that the reference to a transition between a bleached state and colored state is non-limiting and suggests only one example, among many, of an electrochromic transition that may be implemented. Unless otherwise specified herein (including the foregoing discussion), whenever reference is made to a bleached-colored transition, the corresponding device or process encompasses other optical state transitions such as non-reflective-reflective, transparent-opaque, etc. Further, the term "bleached" refers to an optically neutral state, for example, uncolored, transparent, or translucent. Still further, unless specified otherwise herein, the "color" of an electrochromic transition is not limited to any particular wavelength or range of wavelengths. As understood by those of skill in the art, the choice of appropriate electrochromic and counter electrode materials governs the relevant optical transition.

In embodiments described herein, the electrochromic device reversibly cycles between a bleached state and a colored state. In some cases, when the device is in a bleached state, a potential is applied to the electrochromic stack 320 such that available ions in the stack reside primarily in the counter electrode 310. When the potential on the electrochromic stack is reversed, the ions are transported across the ion conducting layer 308 to the electrochromic material 306 and cause the material to transition to the colored state.

Referring again to FIG. 3A, voltage source 316 may be configured to operate in conjunction with radiant and other environmental sensors. As described herein, voltage source 316 interfaces with a device controller (not shown in this figure). Additionally, voltage source 316 may interface with an energy management system that controls the electrochromic device according to various criteria such as the time of year, time of day, and measured environmental conditions. Such an energy management system, in conjunction with large area electrochromic devices (e.g., an electrochromic window), can dramatically lower the energy consumption of a building.

Any material having suitable optical, electrical, thermal, and mechanical properties may be used as substrate 302. Such substrates include, for example, glass, plastic, and mirror materials. Suitable glasses include either clear or tinted soda lime glass, including soda lime float glass. The glass may be tempered or untempered.

In many cases, the substrate is a glass pane sized for residential window applications. The size of such glass pane can vary widely depending on the specific needs of the residence. In other cases, the substrate is architectural glass. Architectural glass is typically used in commercial buildings, but may also be used in residential buildings, and typically, though not necessarily, separates an indoor environment from an outdoor environment. In certain embodiments, architectural glass is at least 20 inches by 20 inches, and can be much larger, for example, as large as about 80 inches by 120 inches. Architectural glass is typically at least about 2 mm thick, typically between about 3 mm and about 6 mm thick. Of course, electrochromic devices are scalable to substrates smaller or larger than architectural glass. Further, the electrochromic device may be provided on a mirror of any size and shape.

On top of substrate 302 is conductive layer 304. In certain embodiments, one or both of the conductive layers 304 and 314 is inorganic and/or solid. Conductive layers 304 and 314 may be made from a number of different materials, including conductive oxides, thin metallic coatings, conductive metal nitrides, and composite conductors. Typically, conductive layers 304 and 314 are transparent at least in the range of wavelengths where electrochromism is exhibited by the electrochromic layer. Transparent conductive oxides include metal oxides and metal oxides doped with one or more metals. Examples of such metal oxides and doped metal oxides include indium oxide, indium tin oxide, doped indium oxide, tin oxide, doped tin oxide, zinc oxide, aluminum zinc oxide, doped zinc oxide, ruthenium oxide, doped ruthenium oxide and the like. Since oxides are often used for these layers, they are sometimes referred to as "transparent conductive oxide" (TCO) layers. Thin metallic coatings that are substantially transparent may also be used.

The function of the conductive layers is to spread an electric potential provided by voltage source 316 over surfaces of the electrochromic stack 320 to interior regions of the stack, with relatively little ohmic potential drop. The electric potential is transferred to the conductive layers though electrical connections to the conductive layers. In some embodiments, bus bars, one in contact with conductive layer 304 and one in contact with conductive layer 314, provide the electric connection between the voltage source 316 and the conductive layers 304 and 314. The conductive layers 304 and 314 may also be connected to the voltage source 316 with other conventional means.

Overlaying conductive layer 304 is electrochromic layer 306. In some embodiments, electrochromic layer 306 is inorganic and/or solid. The electrochromic layer may contain any one or more of a number of different electrochromic materials, including metal oxides. Such metal oxides include tungsten oxide ($WO_3$), molybdenum oxide ($MoO_3$), niobium oxide ($Nb_2O_5$), titanium oxide ($TiO_2$), copper oxide (CuO), iridium oxide ($Ir_2O_3$), chromium oxide ($Cr_2O_3$), manganese oxide ($Mn_2O_3$), vanadium oxide ($V_2O_5$), nickel oxide ($Ni_2O_3$), cobalt oxide ($Co_2O_3$) and the like. During operation, electrochromic layer 306 transfers ions to and receives ions from counter electrode layer 310 to cause optical transitions.

Generally, the colorization (or change in any optical property—e.g., absorbance, reflectance, and transmittance) of the electrochromic material is caused by reversible ion insertion into the material (e.g., intercalation) and a corresponding injection of a charge balancing electron. Typically some fraction of the ions responsible for the optical transition is irreversibly bound up in the electrochromic material. Some or all of the irreversibly bound ions are used to compensate "blind charge" in the material. In most electrochromic materials, suitable ions include lithium ions (Li+) and hydrogen ions (H+) (that is, protons). In some cases, however, other ions will be suitable. In various embodiments, lithium ions are used to produce the electrochromic phenomena. Intercalation of lithium ions into tungsten oxide ($WO_3-y$ ($0<y\leq \sim 0.3$)) causes the tungsten oxide to change from transparent (bleached state) to blue (colored state).

Referring again to FIG. 3A, in electrochromic stack 320, ion conducting layer 308 is sandwiched between electrochromic layer 306 and counter electrode layer 310. In some embodiments, counter electrode layer 310 is inorganic and/or solid. The counter electrode layer may comprise one or more of a number of different materials that serve as a reservoir of ions when the electrochromic device is in the bleached state. During an electrochromic transition initiated by, for example, application of an appropriate electric potential, the counter electrode layer transfers some or all of the ions it holds to the electrochromic layer, changing the electrochromic layer to the colored state. Concurrently, in the case of NiWO, the counter electrode layer colors with the loss of ions.

In some embodiments, suitable materials for the counter electrode complementary to WO3 include nickel oxide (NiO), nickel tungsten oxide (NiWO), nickel vanadium oxide, nickel chromium oxide, nickel aluminum oxide, nickel manganese oxide, nickel magnesium oxide, chromium oxide ($Cr_2O_3$), manganese oxide ($MnO_2$), and Prussian blue.

When charge is removed from a counter electrode 310 made of nickel tungsten oxide (that is, ions are transported from counter electrode 310 to electrochromic layer 306), the counter electrode layer will transition from a transparent state to a colored state.

In the depicted electrochromic device, between electrochromic layer 306 and counter electrode layer 310, there is the ion conducting layer 308. Ion conducting layer 308 serves as a medium through which ions are transported (in the manner of an electrolyte) when the electrochromic device transitions between the bleached state and the colored state. Preferably, ion conducting layer 308 is highly conductive to the relevant ions for the electrochromic and the counter electrode layers, but has sufficiently low electron conductivity that negligible electron transfer takes place during normal operation. A thin ion conducting layer with high ionic conductivity permits fast ion conduction and hence fast switching for high performance electrochromic devices. In certain embodiments, the ion conducting layer 308 is inorganic and/or solid.

Examples of suitable ion conducting layers (for electrochromic devices having a distinct IC layer) include silicates, silicon oxides, tungsten oxides, tantalum oxides, niobium oxides, and borates. These materials may be doped with different dopants, including lithium. Lithium doped silicon oxides include lithium silicon-aluminum-oxide. In some embodiments, the ion conducting layer comprises a silicate-based structure. In some embodiments, a silicon-aluminum-oxide (SiAlO) is used for the ion conducting layer 308.

Electrochromic device 300 may include one or more additional layers (not shown), such as one or more passive layers. Passive layers used to improve certain optical properties may be included in electrochromic device 300. Passive layers for providing moisture or scratch resistance may also be included in electrochromic device 300. For example, the conductive layers may be treated with anti-reflective or protective oxide or nitride layers. Other passive layers may serve to hermetically seal electrochromic device 300.

Figure 3B:
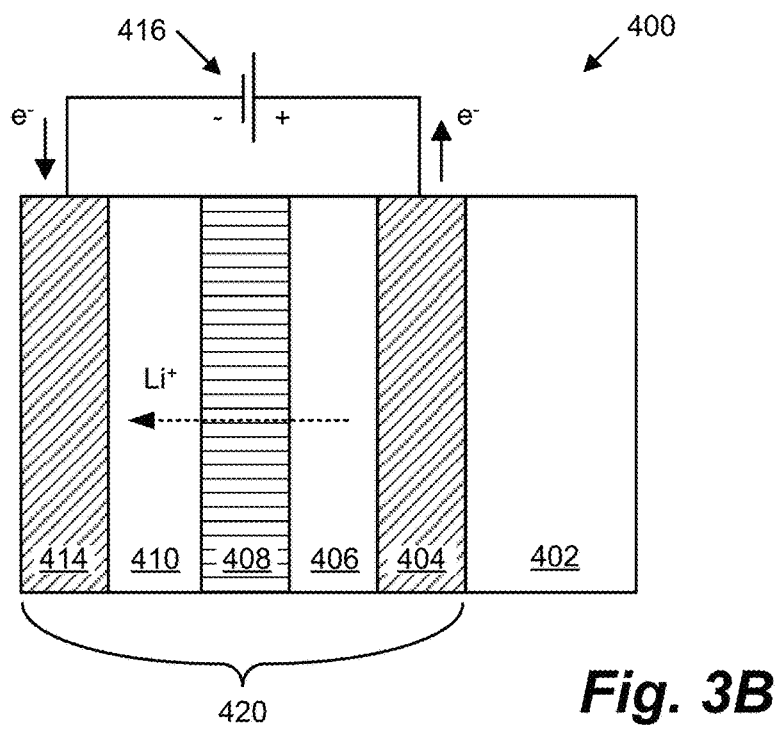
FIG. 3B depicts a schematic cross-section of an electrochromic device in a bleached state (or transitioning to a bleached state).

FIG. 3B is a schematic cross-section of an electrochromic device in a bleached state (or transitioning to a bleached state). In accordance with specific embodiments, an electrochromic device, 400, includes a tungsten oxide electrochromic layer (EC), 406, and a nickel-tungsten oxide counter electrode layer (CE), 410. Electrochromic device 400 also includes a substrate, 402, a conductive layer (CL), 404, an ion conducting layer (IC), 408, and conductive layer (CL), 414.

A power source, 416, is configured to apply a potential and/or current to an electrochromic stack, 420, through suitable connections (e.g., bus bars) to the conductive layers, 404 and 414. In some embodiments, the voltage source is configured to apply a potential of a few volts in order to drive a transition of the device from one optical state to another. The polarity of the potential as shown in FIG. 3A is such that the ions (lithium ions in this example) primarily reside (as indicated by the dashed arrow) in nickel-tungsten oxide counter electrode layer 410.

Figure 3C:
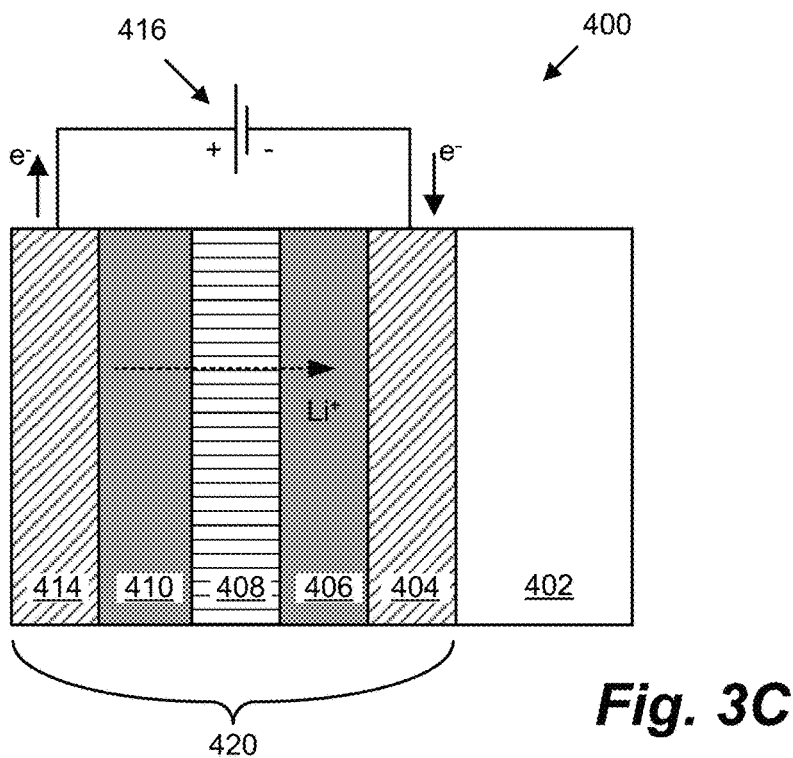
FIG. 3C depicts a schematic cross-section of the electrochromic device shown in FIG. 3B, but in a colored state (or transitioning to a colored state).

FIG. 3C is a schematic cross-section of electrochromic device 400 shown in FIG. 3B but in a colored state (or transitioning to a colored state). In FIG. 3C, the polarity of voltage source 416 is reversed, so that the electrochromic layer is made more negative to accept additional lithium ions, and thereby transition to the colored state. As indicated by the dashed arrow, lithium ions are transported across ion conducting layer 408 to tungsten oxide electrochromic layer 406. Tungsten oxide electrochromic layer 406 is shown in the colored state. Nickel-tungsten oxide counter electrode 410 is also shown in the colored state. As explained, nickel-tungsten oxide becomes progressively more opaque as it gives up (deintercalates) lithium ions. In this example, there is a synergistic effect where the transition to colored states for both layers 406 and 410 are additive toward reducing the amount of light transmitted through the stack and substrate.

As described above, an electrochromic device may include an electrochromic (EC) electrode layer and a counter electrode (CE) layer separated by an ionically conductive (IC) layer that is highly conductive to ions and highly resistive to electrons. As conventionally understood, the ionically conductive layer therefore prevents shorting between the electrochromic layer and the counter electrode layer. The ionically conductive layer allows the electrochromic and counter electrodes to hold a charge and thereby maintain their bleached or colored states. In electrochromic devices having distinct layers, the components form a stack which includes the ion conducting layer sandwiched between the electrochromic electrode layer and the counter electrode layer. The boundaries between these three stack components are defined by abrupt changes in composition and/or microstructure. Thus, the devices have three distinct layers with two abrupt interfaces.

In accordance with certain embodiments, the counter electrode and electrochromic electrodes are formed immediately adjacent one another, sometimes in direct contact, without separately depositing an ionically conducting layer. In some embodiments, electrochromic devices having an interfacial region rather than a distinct IC layer are employed. Such devices, and methods of fabricating them, are described in U.S. patent application Ser. Nos. 12/772, 055 and 12/772,075, each filed on Apr. 30, 2010, and in U.S. patent application Ser. Nos. 12/814,277 and 12/814,279, each filed on Jun. 11, 2010—each of the four applications is entitled "Electrochromic Devices," each names Zhongchun Wang et al. as inventors, and each is incorporated by reference herein in its entirety.

Window Controllers and Control Algorithms

A window controller is used to control the state (i.e., bleached, neutral or some level of coloration) of the electrochromic device of an electrochromic window. In some embodiments, the window controller is able to transition the electrochromic window between two states, a bleached state and a colored state. In other embodiments, the controller can additionally transition the electrochromic window (e.g., having a single electrochromic device) to intermediate coloration states. Certain electrochromic windows allow intermediate coloration levels by using two electrochromic lites in a single IGU, where each lite is a two-state lite. This is described in more detail below.

As noted above with respect to FIGS. 2A and 2B, in some embodiments, an electrochromic window can include an electrochromic device on one lite of an IGU and another electrochromic device on the other lite of an IGU. If the window controller is able to transition each electrochromic device between two states, a bleached state and a colored state, the electrochromic window is able to attain four different states, a colored state with both electrochromic devices being colored, a first intermediate state with one electrochromic device being colored, a second intermediate state with the other electrochromic device being colored, and a bleached state with both electrochromic devices being bleached. Embodiments of multi-pane electrochromic windows are further described in U.S. patent application Ser. No. 12/851,514, naming Friedman et al. as inventors, titled "MULTI-PANE ELECTROCHROMIC WINDOWS" and filed on Aug. 5, 2010, which is incorporated herein by reference in its entirety and for all purposes.

In some embodiments, the window controller is able to transition an electrochromic window having an electrochromic device capable of transitioning between two or more states. For example, a window controller may be able to transition the electrochromic window to a bleached state, an intermediate state, and a colored state. In some other embodiments, the window controller is able to transition an electrochromic window incorporating an electrochromic device between any number of states between the bleached state and the colored state. Embodiments of methods and controllers for transitioning an electrochromic window to an intermediate state or states are further described in U.S. patent application Ser. No. 13/049,623, naming Mehtani et al. as inventors, titled "CONTROLLING TRANSITIONS IN OPTICALLY SWITCHABLE DEVICES" and filed on Mar. 16, 2011, which is incorporated herein by reference in its entirety and for all purposes.

In some embodiments, a window controller can power one or more electrochromic devices in an electrochromic window. Typically, this function of the window controller is augmented with one or more other functions described in more detail below. Window controllers described herein are not limited to those that have the function of powering an electrochromic device to which it is associated for the purposes of control. That is, the power source for the electrochromic window may be separate from the window controller, where the controller has its own power source and directs application of power from the window power source to the window. However, it is convenient to include a power source with the window controller and to configure the controller to power the window directly, because it obviates the need for separate wiring for powering the electrochromic window.

Further, the window controllers described in this section are described as standalone controllers which may be configured to control the functions of a single window or a plurality of electrochromic windows, without integration of the window controller into a building control network or a building management system (BMS). Window controllers, however, may be integrated into a building control network or a BMS, as described further in the Building Management System section of this disclosure.

Figure 4:
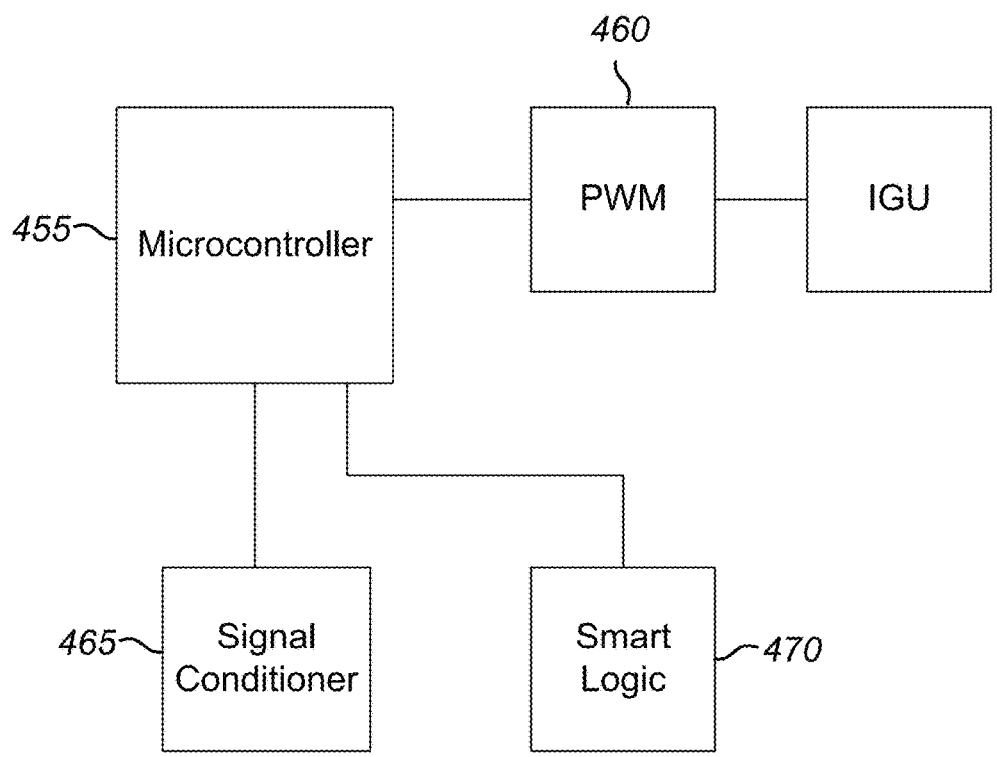
FIG. 4 depicts a block diagram of a window controller.

FIG. 4 depicts a block diagram of a window controller. FIG. 4 is a simplified block diagram of a window controller, and more detail regarding window controllers can be found in related U.S. patent application Ser. No. 13/449,248, naming Brown as inventor, titled "CONTROLLER FOR OPTICALLY SWITCHABLE WINDOWS" and filed on Apr. 17, 2012, and in U.S. patent application Ser. No. 13/449,251, naming Brown as inventor, titled "CONTROLLER FOR DRIVING OPTICAL TRANSITIONS IN MULTIPLE WINDOW TYPES" and filed on Apr. 17, 2012, both of which are incorporated herein by reference in their entireties and for all purposes. As shown in FIG. 4, a window controller, 450, includes a microcontroller, 455, a power width modulator (PWM), 460, a signal conditioning module, 465, and a smart logic module, 470.

FIG. 5 depicts a schematic diagram of a room including an electrochromic window and a plurality of sensors. In some embodiments, output from these sensors may be input to a signal conditioning module, 465, of a window controller, 450. In some other embodiments, output from these sensors may be input to a network including a building management system, as described further below in the Building Management System section. Although the various sensors are depicted as being, e.g., on a vertical surface of the room, this is for the sake of simplicity, and any or all of the sensors may be on the ceiling or the floor as well.

A room, 500, includes an electrochromic window, 505. Electrochromic window 505 is between the exterior and the interior of a building which includes room 500. Window controller 450 is connected to and configured to control the optical state of electrochromic window 505. The sensors in room 500 include an exterior photosensor, 510, an exterior temperature sensor, 515, an interior photosensor, 520, an interior transmissivity sensor, 525, an occupancy sensor, 530, and a power meter, 535. Each of these sensors is described briefly, below.

Exterior photosensor 510 and interior photosensor 520 are devices that are able to detect the irradiance of light incident upon them. Light incident upon a photosensor may be light directly from a light source or light reflected from a surface to the photosensor. Exterior photosensor 510 generally measures the direct or reflected sunlight incident upon the photosensor. A light level detected by exterior photosensor 510 changes with the time of day and with the time of year as the angle at which sunlight strikes the earth changes. The light level detected by exterior photosensor 510 also changes with the weather; e.g., on cloudy days, sunlight would be blocked by the clouds and the light level detected by exterior photosensor 510 would be lower than on cloudless days. In some embodiments, there may be one or more exterior photosensors 510. Output from the one or more exterior photosensors 510 could be compared to one another to determine, for example, if one of exterior photosensors 510 is shaded by an object, such as by a bird that landed on exterior photosensor 510.

Interior photosensor 520 generally measures the ambient light in room 500. In some embodiments, interior photosensor measures the light reflected from a surface in the field of view of interior photosensor 520. With the same lighting of room 500, interior photosensor 520 would measure a higher light level when a piece of white paper is in the field of view of interior photosensor 520 than when, e.g., a piece of colored carpet is in the field of view of interior photosensor 520, for example, due to the higher reflectivity of the white paper. Because of this, if interior photosensor 520 is moved or if the object(s) in the field of view of interior photosensor 520 is changed, the output of interior photosensor 520 may change. Thus, in some embodiments, window controller 450 may perform a recalibration routine to determine the output range of interior photosensor 520, which again depends on the object(s) in the field of view interior photosensor 520. Such a recalibration routine may be performed according to set schedule (e.g., once a week) or triggered by a person (e.g., a maintenance person who rearranges the furniture in room 500).

Exterior photosensor 510 and interior photosensor 520 may be any number of different types of photosensors. For example, exterior photosensor 510 and interior photosensor 520 can be charge coupled devices (CCDs), photodiodes, photoresistors, or photovoltaic cells. One of ordinary skill in the art would appreciate that future developments in photosensor technology would also work, as they measure light intensity and provide an electrical output representative of the light level.

Exterior temperature sensor 515 is a device able to measure the outside temperature. Exterior temperature sensor 515 can be any number of different temperature sensors, including a thermocouple, a thermistor, or a resistance temperature detector. In some embodiments, room 500 further includes an interior temperature sensor.

Interior transmissivity sensor 525 is a device able to measure the amount of light transmitted though electrochromic window 505. In some embodiments, interior transmissivity sensor 525 is a photosensor, which may be similar to exterior photosensor 510 or interior photosensor 520, with the field of view of the sensor oriented to be facing electrochromic window 505 in order to measure incident light passing through electrochromic window 505. By combining the measurement of exterior photosensor 510 with a photosensor having a field of view facing the interior of electrochromic window 505, the transmissivity of electrochromic window 505 can be determined.

Occupancy sensor 530 is a device able to detect when a person is in room 500. Occupancy sensors are usually motion sensors; when occupancy sensor 530 detects motion, it is assumed that a person in in room 500, and when occupancy sensor 530 does not detect motion, it is assumed that a person in not in room 500. Occupancy sensors may be set so that it is assumed that a person is in a room for a period of time after the last motion was detected; this can account for a person sitting at a desk and not moving very much, but still being in the room. In some embodiments, the occupancy sensor may be a motion sensor used to control the lights lighting the room. Occupancy sensor 530 can use, for example, infrared (IR) technology, acoustic technology, or a combination of the two. The field of view of occupancy sensor 530 may be selected/adjusted so that it responds to motion in room 500 and not to motion outside of room 500 (e.g., motion outside of the building housing room 500 or motion in a hallway of the building housing room 500).

Power meter 535 is a device able to measure the power consumption of room 500. The power consumption of room 500 may include heating, ventilation, and air conditioning systems (HVAV systems) and lighting. In some embodiments, power meter 535 includes devices able to interface with the wires of the circuits providing power to room 500. Power meter may be able to separately measure the power consumed by the interior lighting of room 500 and the power consumed by HVAC system of room 500 if the interior lighting and HVAC system are on different circuits of room 500.

In some embodiments, when window controller 450 is not connected to a network, two or more sensors may provide output signals to window controller 450 through signal conditioning module 465. Signal conditioning module 465 passes these output signals to a microcontroller, 455. Microcontroller 455 determines the level of tint of electrochromic window 505, based on the outputs, and instructs a PWM, 460, to apply a voltage and/or current to electrochromic window 505 to transition to the desired state.

In some embodiments, output from exterior photosensor 510, interior photosensor 520, a temperature sensor, and a tint command are input to signal conditioning module 465. The temperature sensor may be an interior temperature sensor (not shown) or exterior temperature sensor 515. The tint command may be a command from a person or occupant in room 500 as to the tint level desired by the person. For example, depending on electrochromic window 505, the person may instruct the window to transition to a bleached state, a colored state, or an intermediate state. Such tint command instructions may be made, for example, with a wireless remote or with a panel associated with window controller 450. If room 500 is a bedroom, for example, the person may want electrochromic window 505 to be in a colored state at night for privacy.

In some embodiments, the tint command input may be a voltage signal to signal conditioning module 465 of about 0 V to about 10 V. A tint command input of 0 V to 4.9 V may indicate a command for electrochromic window 505 to transition to a beached state and a tint command input of 5 V to about 10 V may indicate a command for electrochromic window 505 to transition to a colored state. As another example, when the electrochromic window 505 has four states, a tint command input of 0 V to 2.5 V may indicate a command for electrochromic window 505 to transition to a beached state, a tint command input of 2.6 V to 5 V may indicate a command for electrochromic window 505 to transition to a first intermediate state, a tint command input of 5.1 V to 7.5 V may indicate a command for electrochromic window 505 to transition to a second intermediate state, and a tint command input of 7.6 V to about 10 V may indicate a command for electrochromic window 505 to transition to a colored state.

The output signals from the sensors and the tint command are passed to microcontroller 455. Whether or not electrochromic window 505 transitions to a state as indicated by the tint command will depend on how microcontroller 455 is configured to process outputs from exterior photosensor 510, interior photosensor 520, and the temperature sensor, in relation to the tint command. For example, in some embodiments, the tint command input may override the output from exterior photosensor 510, interior photosensor 520, and the temperature sensor and electrochromic window 505 may transition to a state indicated by the tint command input. Microcontroller 455 instructs PWM 460 to supply current and/or voltage to transition electrochromic window 505 according to the tint command input.

In some embodiments, microcontroller 455 may employ any one or more of various logic functions or algorithms to arrive at tint decisions based on signals from the sensors and/or other input. The sensor outputs may serve as independent variables to a linear or non-linear expression, a look up table, a tree, etc. In some embodiments, microcontroller 455 uses a function to determine the current and/or voltage that power width modulator 460 should send to electrochromic window 505. An example of one function is shown in FIG. 6.

FIG. 6 depicts a function that uses weighting constants, k1, k2, k3, and k4 to weight the outputs from the different sensors/commands, where EP is the exterior photosensor output, IP is the interior photosensor output, T is the temperature sensor output, and TC is the tint command input. The weighting constants are set to achieve the desired response for electrochromic window 505. Using the function, an output value (OV) is determined. Depending on the output value, the microcontroller 455 can instruct PWM 460 to transition electrochromic window 505 to a desired state.

For example, when the output value ranges from 0 to 15 (e.g., 16 tint states, ranging from about 67% transmissivity to 4% transmissivity) and electrochromic window 505 has two states, with an output value of 0, window controller 450 can instruct electrochromic window 505 to transition to a bleached state, and with an output value of 15, window controller 450 can instruct electrochromic window 505 to transition to a colored state. As another example, when the output value ranges from 0 to 15 and electrochromic window 505 has four states, with an output value of 0 to 4, window controller 450 can instruct electrochromic window 505 to transition to a bleached state, with an output value of 5 to 9, window controller 450 can instruct electrochromic window 505 to transition to a first intermediate state, with an output value of 10 to 14, window controller 450 can instruct electrochromic window 505 to transition to a second intermediate state, and with an output value of 15, window controller 450 can instruct electrochromic window 505 to transition to a colored state. As yet another example, when the output value ranges from 0 to 15 and electrochromic window 505 has an infinite number of intermediate states, with an output value of 0, window controller 450 can instruct electrochromic window 505 to transition to a bleached state, with an output value of 15, window controller 450 can instruct electrochromic window 505 to transition to a colored state, and with an output value between 0 to 15, window controller 450 can instruct electrochromic window 505 to transition to a tint level corresponding to the output value.

The weighting constants, k1, k2, k3, and k4 are set to achieve the desired response for electrochromic window 505. For example, if an occupant in the room is to have control over the tint level of electrochromic window 505, the weighting constants are set to k1=0, k2=0, k3=0, and k4=1. Weighting constant k3 (i.e., for the exterior temperature sensor output) may be given a large value if electrochromic window 505 is used to reduce HVAC energy consumption in room 500. Weighting constants k1 and k2 (i.e., for the exterior photosensor output and the interior photosensor output, respectively) may be given values to keep the lighting in room 500 relatively constant. The weighting constants may be set to achieve any of a number of different responses for electrochromic window 505.

In some embodiments, weighting constants, k1, k2, k3, and k4 may change according to an external influence or a schedule. Examples of external influences that may cause the constants to vary include changes in the weather and changes in the power consumption conditions within a building or across a geographic area (which may be noted by a communication from a power utility company). In some embodiments, the schedule may be a daily schedule, and in some other embodiments, the schedule may be a yearly schedule. In some embodiments, the schedule may be a schedule that includes different daily schedules for different times of the year. For example, the daily schedule may change for the different seasons of the year, i.e., winter, spring, summer, and fall.

An example of one schedule is shown in FIG. 7. For example, schedule 1 may be a schedule for 10 pm to 6 am, schedule 2 may be a schedule for 10 am to 1 pm, and schedule 3 may be a schedule for 1 pm to 10 pm. When room 500 is a room in a residential home, schedule 1 may color electrochromic window 505 for privacy, and schedules 2 and 3 may balance the light in room 500 and the temperature.

As another example, schedule 1 may be a schedule for the winter, schedule 2 may be a schedule for the spring and the summer, and schedule 3 may be a schedule for the fall. Schedules 1, 2, and 3 may balance the light and the temperature in room 500, taking into account the different seasons, including, for example, concomitant changes in average temperature, angle and location of the sun, precipitation patterns, and the like.

FIGS. 6 and 7 show one embodiment of a relationship for determining the tint level that window controller 450 may use. More outputs from different sensors can be input to signal conditioning module 465 and the function and weighting constants of the function may be adjusted appropriately. Also, fewer outputs can be input to signal conditioning module 465. In some other embodiments, the relationship used for determining a level of tint is a lookup table in which levels of tint are specified for various combinations of output signal values.

Figure 8:
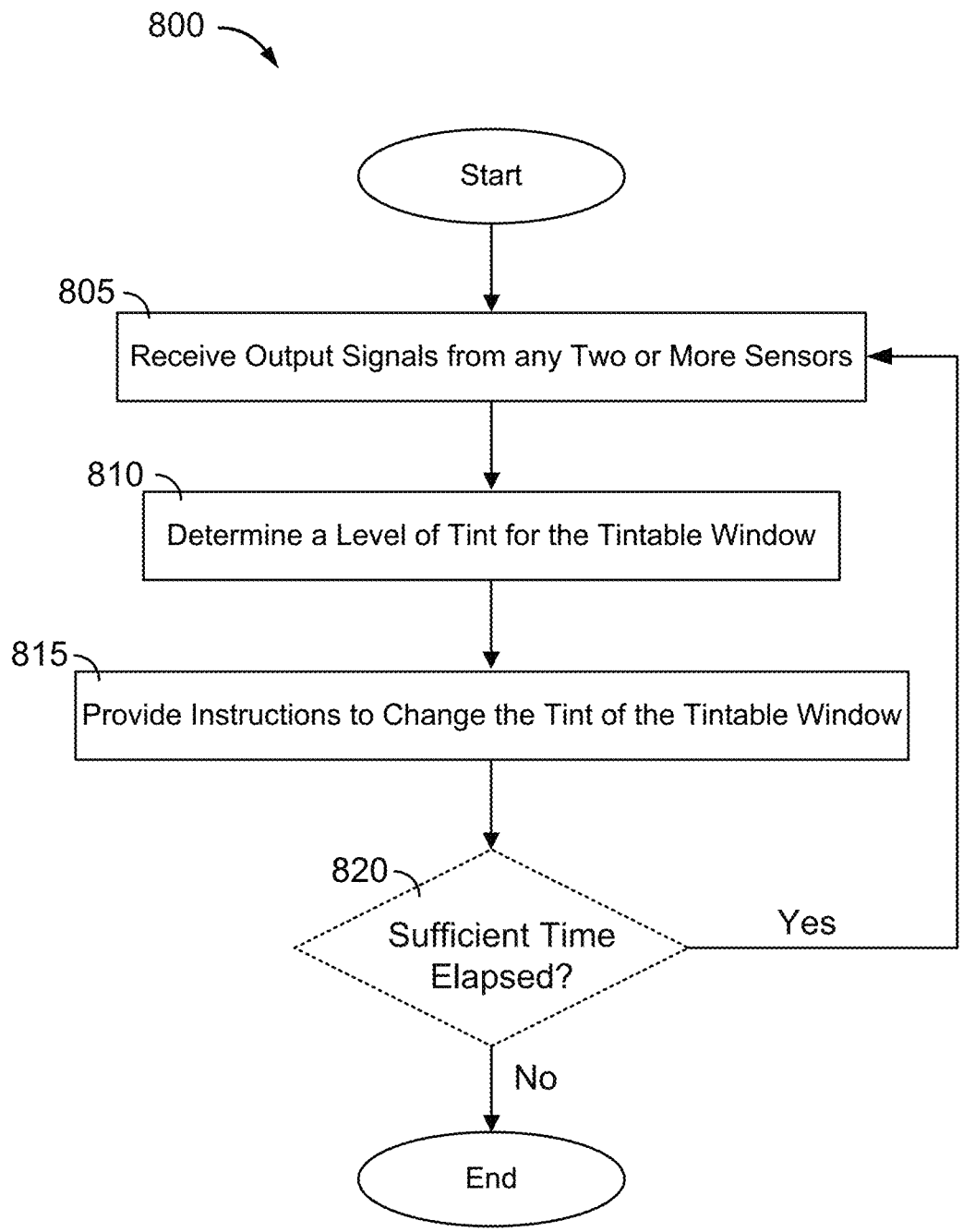
FIG. 8 shows a flow chart of a method for limiting energy consumption in a room having at least one tintable window between an interior and exterior of the room.

FIG. 8 shows a flow chart of a method for limiting the energy consumption in a room having at least one tintable window between an interior and exterior of the room. The level of tinting may be controlled automatically; i.e., output from the sensors may be input to the window controller, and the window controller may control the tint state of the tintable window according to the output from the sensors.

As shown in FIG. 8, in operation 805, output signals from any two or more sensors are received. In some embodiments, output from the sensors is received by a window controller. In some other embodiments, output from these sensors is received at a network including a building management system or a master network controller. Again, building management systems are described further below in the Building Management System section. The sensors may be selected from the group consisting of an exterior photosensor, an interior photosensor, an occupancy sensor, an exterior temperature sensor, and a transmissivity sensor which detects light passing through the tintable window from the exterior. In some embodiments, when the interior photosensor is facing the tintable window, output from both the exterior photosensor and the interior photosensor can be used to determine the light passing through the tintable window from the exterior.

In some embodiments, output indicating an energy or power consumption by a heating system, a cooling system, and/or lighting in the room also is received. In some embodiments, devices that interface with the wires of the circuits providing power to the room including the tintable window provide the energy or power consumption output.

In operation 810, a level of tint for the tintable window is determined using a relationship between the received energy output signals and the level of tint. In some embodiments, the relationship tends to minimize energy consumption by a heating system, a cooling system, and/or lighting in the room while providing conditions suitable for occupancy of the room. For example, when output indicating an energy or power consumption by a heating system, a cooling system, and/or lighting in the room is received, this output may be used with the other received output signals in to determine the level of tinting for the tintable window to minimize energy consumption.

In some embodiments, the relationship is an expression in which the level of tint is the dependent variable and the output signals are independent variables; an example of such a relationship is shown in FIG. 6. The window controller receives the output signals and computes the level of tint based on the relationship and the output signals. In some other embodiments, the relationship is a lookup table in which levels of tint are specified for various combinations of output signal values. Such a lookup table may be used, for example, when the tintable window is capable of achieving a finite number of states (e.g., two states, bleached and colored, or four states).

In some embodiments of method 800, the output signals include a signal from an exterior photosensor. The relationship employed in operation 810 requires transitioning from a first darker tint level to a second lighter tint level when the output signal from the exterior photosensor passes a first threshold. The relationship employed in operation 810 also requires transitioning from the second lighter tint level to the first darker tint level when the output signal from the exterior photosensor passes a second threshold. These embodiments are described further below with respect to FIGS. 9 and 10.

Referring again to FIG. 8, in operation 815, instructions are provided to change the tint of the tintable window to the level of tint determined in operation 810. In some embodiments, this includes a window controller applying voltage or current to the tintable window to drive the change in tint pursuant to the instructions. For example, for window controller 450 shown in FIG. 4, microcontroller 455 provides instruction to PWM 460 to apply voltage and/or current to the tintable window.

Method 800 can be implemented in an iterative process, as described in operation 820, a decision block. For example, as part of an automated program to control one or more electrochromic windows, the tint level instructions may be generated based on a preset timing function, where after a preset time has elapsed, the controller samples output from the sensors in order to generate new instructions for the window. If the time period has not elapsed, then no further instructions are needed and the method ends. Once the time period has elapsed, then operations 805 through 815 are repeated. Decision block 820 may also be based on any number of criteria, depending on the desired control level of the one or more windows. For example, decision block 820 may query whether there has been any change in the output from one or more sensors. If the answer is negative, then the method is complete; if the answer is affirmative, then operations 805 through 815 are repeated.

Figure 9:
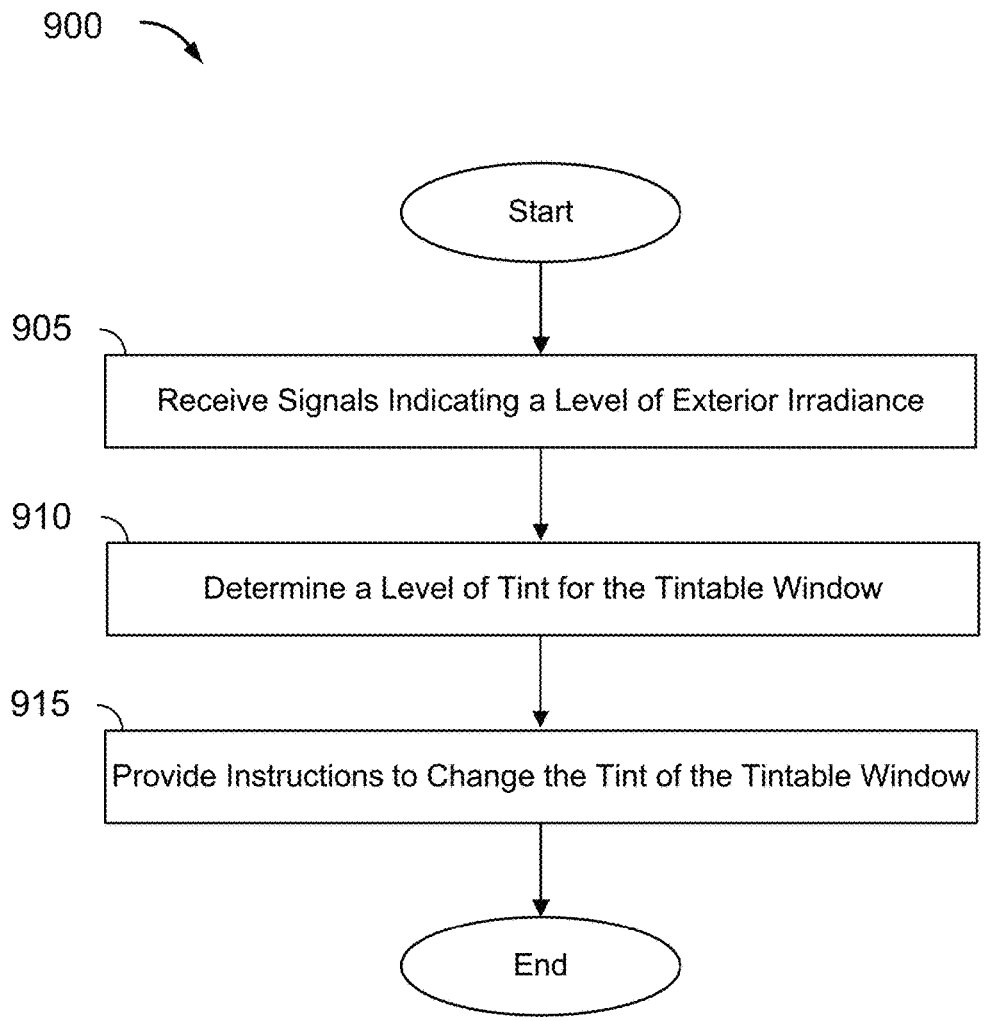
FIG. 9 shows a flow chart of a method of operating a tintable window installed between an interior and exterior of a room.

FIG. 9 shows a flow chart of a method, 900, of operating a tintable window installed between an interior and exterior of a room. The level of tinting may be controlled automatically; i.e., output from the sensors may be input to the window controller, and the window controller may control the tint state of the tintable window according to the output from the sensors.

Figure 10:
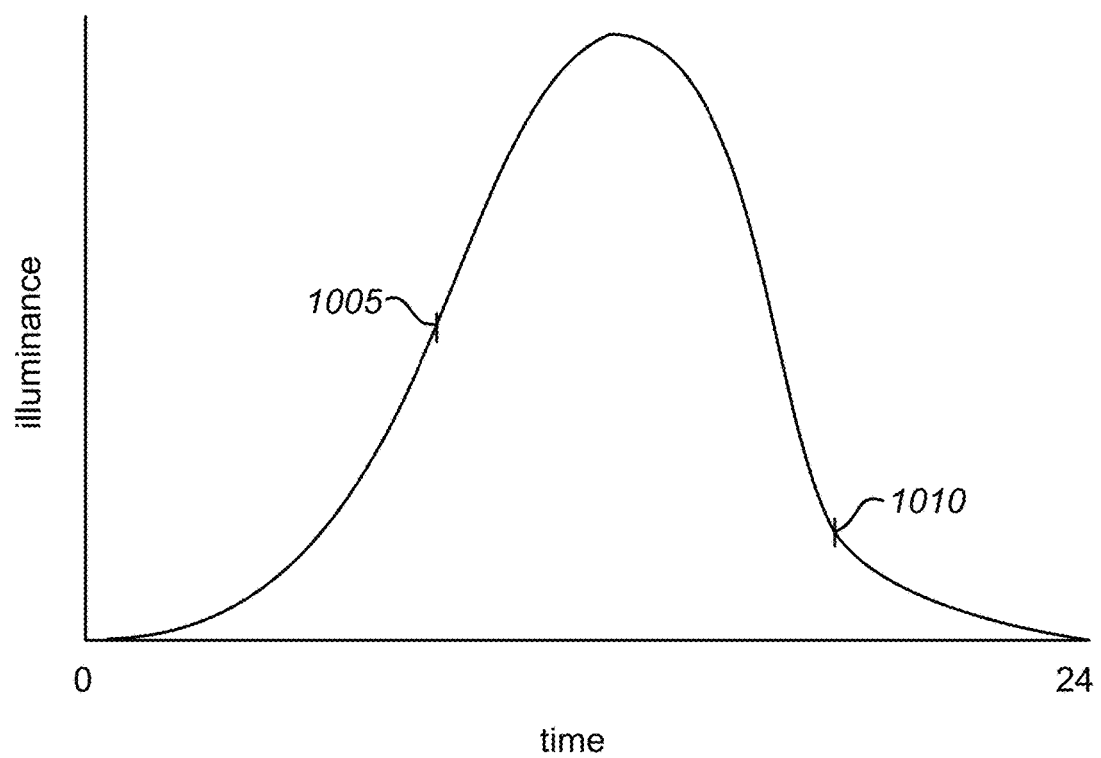
FIG. 10 shows a plot of illuminance versus time for an exterior photosensor over a 24-hour period.

In operation 905 of method 900 shown in FIG. 9, signals indicating a level of exterior irradiance received at or proximate to the tintable window are received. The exterior photosensor measures the amount of light incident upon the photosensor, or the irradiance. Illuminance is closely related to irradiance; illuminance is a measure of the intensity of illumination on a surface. Irradiance, however, is based on physical power, with all wavelengths being weighted equally, while illuminance takes into account that the human eye's visual system is more sensitive to some wavelengths than others, and accordingly every wavelength is given a different weight. FIG. 10 shows a plot of illuminance versus time for a 24-hour period, with the time starting at 0 (i.e., 12 AM) and ending 24 hours later. As shown, the illuminance is low at 0, then increases with time until about midday, reaching a maximum at midday, and then decreases throughout the remainder of the day.

In operation 910, a level of tint for the tintable window is determined using a relationship between the received output signals and the level of tint. The relationship employed in operation 910 requires transitioning from a first lighter tint level to a second darker tint level when the output signal from the exterior photosensor passes a first threshold, 1005. The relationship employed in operation 910 also requires transitioning from the second darker tint level to the first lighter tint level when the output signal from the exterior photosensor passes a second threshold, 1010. First threshold 1005 and second threshold 1010 are different levels of irradiance/illuminance. For example, in some embodiments, the level of irradiance/illuminance at second threshold 1010 is lower than the level of irradiance/illuminance at first threshold 1005.

In operation 915, instructions are provided to change the tint of the tintable window to the level of tint determined in operation 910. In some embodiments, operation 915 is similar to operation 815 described with respect to FIG. 8.

Method 900 of controlling the tint state of a tintable window may maximize energy savings for the room including the tintable window. For example, the room may be lit by sunlight in the early morning, minimizing lighting energy. As the sun's position changes and temperature in the room starts to increase due to sunlight though the tintable window, the HVAC power used for cooling the room increases, and the tintable window is transitioned at first threshold 1005. Then, when the sun begins to set and the sunlight though the tintable window decreases the HVAC power used for cooling, the tintable window is transitioned at second threshold 1010, which may reduce the lighting energy.

Analogous to method 800, method 900 may include a decision block as in method 800. For example, the decision to repeat operations 905-915 may be based on a preset timing event; for example, knowing the expected illumination during a 24 hour period, the illumination is sampled according to a preset schedule. In another example, if a change in illumination level as read by the photosensor meets a certain threshold value, then new tint instructions are generated and provided to the window(s) based on this change in illumination.

The methods shown in FIGS. 8 and 9 are two methods of controlling the tint state of a tintable window. Many other methods of controlling the tint state of a tintable window are possible, using different combinations of sensors and weighting the output of the different sensors using weighting functions.

Building Management Systems

The window controllers described herein also are suited for integration with a BMS. A BMS is a computer-based control system installed in a building that monitors and controls the building's mechanical and electrical equipment such as ventilation, lighting, power systems, elevators, fire systems, and security systems. A BMS consists of hardware, including interconnections by communication channels to a computer or computers, and associated software for maintaining conditions in the building according to preferences set by the occupants and/or by the building manager. For example, a BMS may be implemented using a local area network, such as Ethernet. The software can be based on, for example, internet protocols and/or open standards. One example of software is software from Tridium, Inc. (of Richmond, Va.). One communications protocol commonly used with a BMS is BACnet (building automation and control networks).

A BMS is most common in a large building, and typically functions at least to control the environment within the building. For example, a BMS may control temperature, carbon dioxide levels, and humidity within a building. Typically, there are many mechanical devices that are controlled by a BMS such as heaters, air conditioners, blowers, vents, and the like. To control the building environment, a BMS may turn on and off these various devices under defined conditions. A core function of a typical modern BMS is to maintain a comfortable environment for the building's occupants while minimizing heating and cooling costs/demand. Thus, a modern BMS is used not only to monitor and control, but also to optimize the synergy between various systems, for example, to conserve energy and lower building operation costs. In some embodiments, a window controller is integrated with a BMS, where the window controller is configured to control one or more tintable or electrochromic windows. In one embodiment, the one or more electrochromic windows include at least one all solid state and inorganic electrochromic device. In one embodiment, the one or more electrochromic windows include only all solid state and inorganic windows. In one embodiment, the electrochromic windows are multistate electrochromic windows, as described in U.S. patent application Ser. No. 12/851,514, filed on Aug. 5, 2010, and entitled "Multipane Electrochromic Windows."

Figure 11:
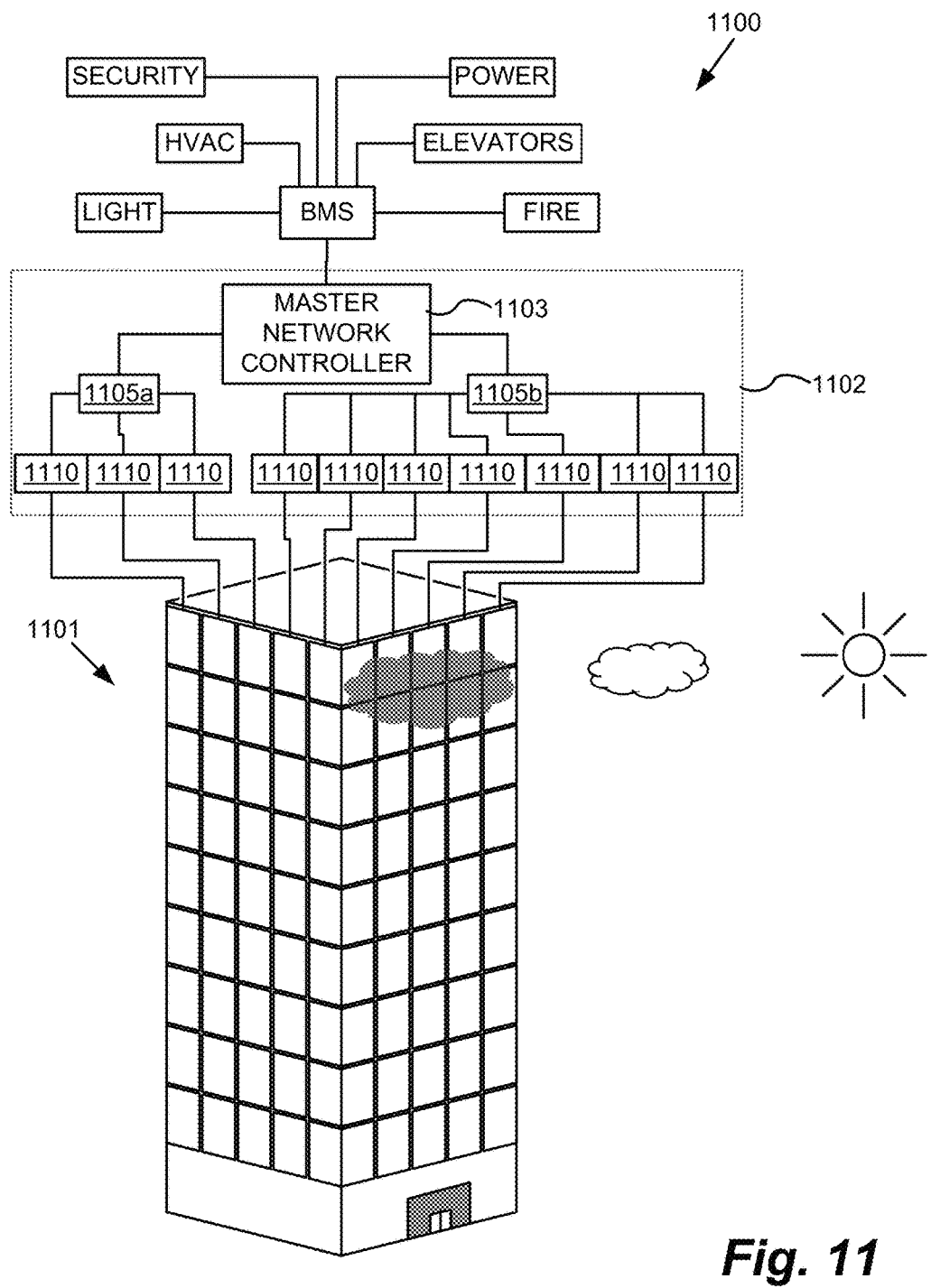
FIG. 11 depicts a schematic diagram of an embodiment of a building management system.

FIG. 11 depicts a schematic diagram of an embodiment of a BMS, 1100, that manages a number of systems of a building, 1101, including security systems, heating/ventilation/air conditioning (HVAC), lighting of the building, power systems, elevators, fire systems, and the like. Security systems may include magnetic card access, turnstiles, solenoid driven door locks, surveillance cameras, burglar alarms, metal detectors, and the like. Fire systems may include fire alarms and fire suppression systems including a water plumbing control. Lighting systems may include interior lighting, exterior lighting, emergency warning lights, emergency exit signs, and emergency floor egress lighting. Power systems may include the main power, backup power generators, and uninterrupted power source (UPS) grids.

Also, BMS 1100 manages a window controller, 1102. In this example, window controller 1102 is depicted as a distributed network of window controllers including a master network controller, 1103, intermediate network controllers, 1105a and 1105b, and end or leaf controllers, 1110. End or leaf controllers 1110 may be similar to window controller 450 described with respect to FIG. 4. For example, master network controller 1103 may be in proximity to the BMS, and each floor of building 1101 may have one or more intermediate network controllers 1105a and 1105b, while each window of the building has its own end controller 1110. In this example, each of controllers 1110 controls a specific electrochromic window of building 1101.

Each of controllers 1110 can be in a separate location from the electrochromic window that it controls, or be integrated into the electrochromic window. For simplicity, only ten electrochromic windows of building 1101 are depicted as controlled by window controller 1102. In a typical setting there may be a large number of electrochromic windows in a building controlled by window controller 1102. Window controller 1102 need not be a distributed network of window controllers. For example, a single end controller which controls the functions of a single electrochromic window also falls within the scope of the embodiments disclosed herein, as described above. Advantages and features of incorporating electrochromic window controllers as described herein with BMS's are described below in more detail and in relation to FIG. 11, where appropriate.

One aspect of the disclosed embodiments is a BMS including a multipurpose electrochromic window controller as described herein. By incorporating feedback from a electrochromic window controller, a BMS can provide, for example, enhanced: 1) environmental control, 2) energy savings, 3) security, 4) flexibility in control options, 5) improved reliability and usable life of other systems due to less reliance thereon and therefore less maintenance thereof, 6) information availability and diagnostics, 7) effective use of staff, and various combinations of these, because the electrochromic windows can be automatically controlled.

In some embodiments, a BMS may not be present or a BMS may be present but may not communicate with a master network controller or communicate at a high level with a master network controller. In some embodiments, a master network controller can provide, for example, enhanced: 1) environmental control, 2) energy savings, 3) flexibility in control options, 4) improved reliability and usable life of other systems due to less reliance thereon and therefore less maintenance thereof, 5) information availability and diagnostics, 6) effective use of staff, and various combinations of these, because the electrochromic windows can be automatically controlled. In these embodiments, maintenance on the BMS would not interrupt control of the electrochromic windows.

Figure 12:
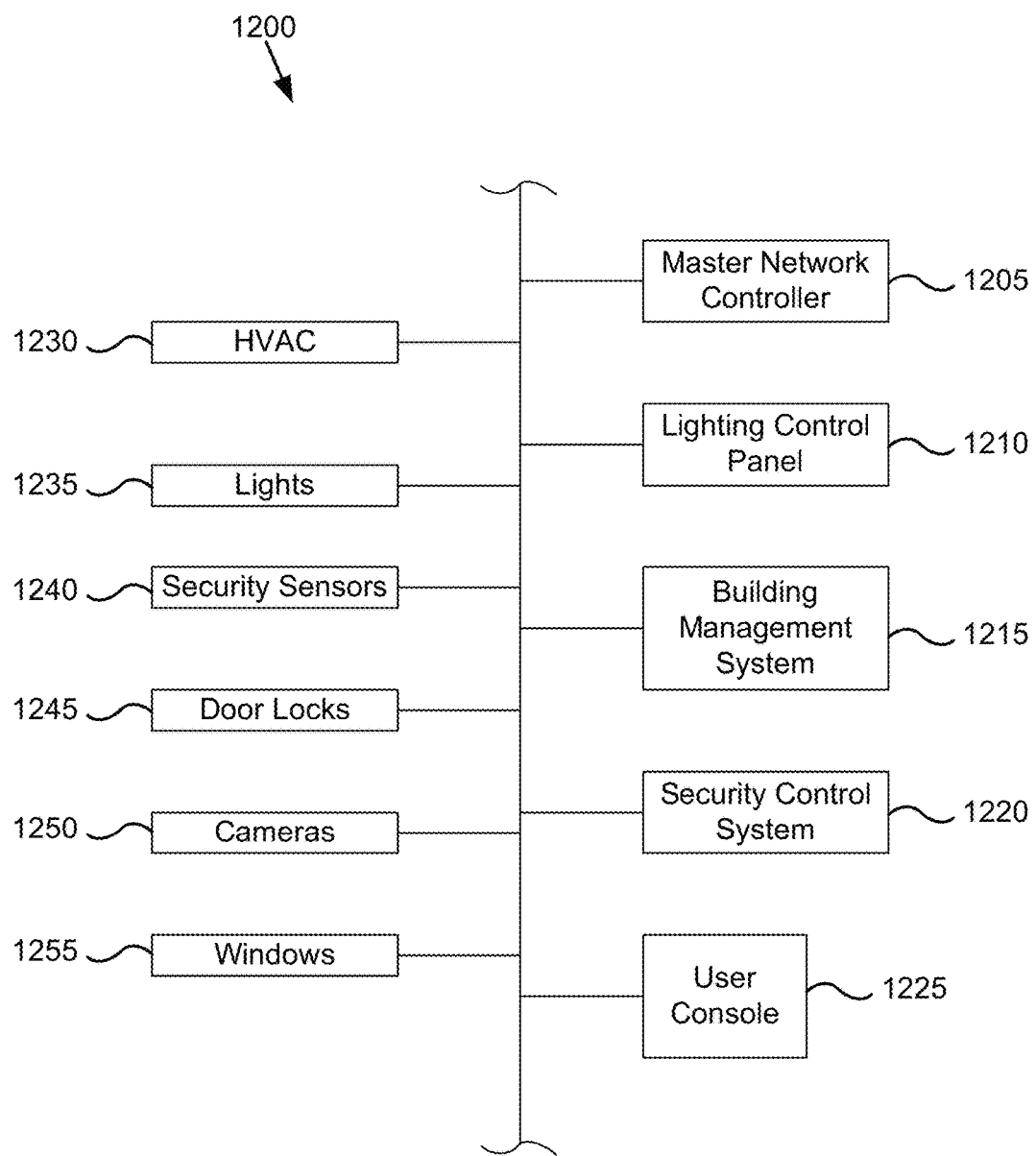
FIG. 12 depicts a block diagram of an embodiment of a building network.

FIG. 12 depicts a block diagram of an embodiment of a building network, 1200, for a building. As noted above, network 1200 may employ any number of different communication protocols, including BACnet. As shown, building network 1200 includes a master network controller, 1205, a lighting control panel, 1210, a building management system (BMS), 1215, a security control system, 1220, and a user console, 1225. These different controllers and systems in the building may be used to receive input from and/or control a HVAC system, 1230, lights, 1235, security sensors, 1240, door locks, 1245, cameras, 1250, and tintable windows, 1255, of the building.

Master network controller 1205 may function in a similar manner as master network controller 1103 described with respect to FIG. 11. Lighting control panel 1210 may include circuits to control the interior lighting, the exterior lighting, the emergency warning lights, the emergency exit signs, and the emergency floor egress lighting. Lighting control panel 1210 also may include occupancy sensors in the rooms of the building. BMS 1215 may include a computer server that receives data from and issues commands to the other systems and controllers of network 1200. For example, BMS 1215 may receive data from and issue commands to each of the master network controller 1205, lighting control panel 1210, and security control system 1220. Security control system 1220 may include magnetic card access, turnstiles, solenoid driven door locks, surveillance cameras, burglar alarms, metal detectors, and the like. User console 1225 may be a computer terminal that can be used by the building manager to schedule operations of, control, monitor, optimize, and troubleshoot the different systems of the building.

Software from Tridium, Inc., may generate visual representations of data from different systems for user console 1225.

Each of the different controls may control individual devices/apparatus. Master network controller 1205 controls windows 1255. Lighting control panel 1210 controls lights 1235. BMS 1215 may control HVAC 1230. Security control system 1220 controls security sensors 1240, door locks 1245, and cameras 1250. Data may be exchanged and/or shared between all of the different devices/apparatus and controllers that are part of building network 1200.

In some cases, the systems of BMS 1100 or building network 1200 may run according to daily, monthly, quarterly, or yearly schedules. For example, the lighting control system, the window control system, the HVAC, and the security system may operate on a 24 hour schedule accounting for when people are in the building during the work day. At night, the building may enter an energy savings mode, and during the day, the systems may operate in a manner that minimizes the energy consumption of the building while providing for occupant comfort. As another example, the systems may shut down or enter an energy savings mode over a holiday period.

The scheduling information may be combined with geographical information. Geographical information may include the latitude and longitude of the building. Geographical information also may include information about the direction that each side of the building faces. Using such information, different rooms on different sides of the building may be controlled in different manners. For example, for east facing rooms of the building in the winter, the window controller may instruct the windows to have no tint in the morning so that the room warms up due to sunlight shining in the room and the lighting control panel may instruct the lights to be dim because of the lighting from the sunlight. The west facing windows may be controllable by the occupants of the room in the morning because the tint of the windows on the west side may have no impact on energy savings. However, the modes of operation of the east facing windows and the west facing windows may switch in the evening (e.g., when the sun is setting, the west facing windows are not tinted to allow sunlight in for both heat and lighting).

Described below is an example of a building, for example, like building 1101 in FIG. 11, including a building network or a BMS, tintable windows for the exterior windows of the building (i.e., windows separating the interior of the building from the exterior of the building), and a number of different sensors. Light from exterior windows of a building generally has an effect on the interior lighting in the building about 20 feet or about 30 feet from the windows. That is, space in a building that is more that about 20 feet or about 30 feet from an exterior window receives little light from the exterior window. Such spaces away from exterior windows in a building are lit by lighting systems of the building.

Further, the temperature within a building may be influenced by exterior light and/or the exterior temperature. For example, on a cold day and with the building being heated by a heating system, rooms closer to doors and/or windows will lose heat faster than the interior regions of the building and be cooler compared to the interior regions.

For exterior photosensors, the building may include exterior photosensors on the roof of the building. Alternatively, the building may include an exterior photosensor associated with each exterior window (e.g., as described in relation to FIG. 5, room 500) or an exterior photosensor on each side of the building. An exterior photosensor on each side of the building could track the irradiance/illuminance on a side of the building as the sun changes position throughout the day.

For exterior temperature sensors, the building may include exterior temperature sensors at a few locations to determine an average exterior temperature. For interior temperature sensors, each room that has an exterior window may include an interior temperature sensor. Alternatively, a few rooms on each side of the building may include an interior temperature sensor.

For interior photosensors and transmissivity sensors, the building may include interior photosensors and interior transmissivity sensors in each room that has an exterior window. Alternatively, a few rooms on each side of the building may include these sensors.

Each room of the building may include an occupancy sensor that is associated with the lights and/or lighting panel in the room. The building may include power meters for individual rooms or groups of rooms (e.g., a group of rooms having exterior windows on one side of the building). A power meter setup will depend on the circuitry setup of the building, however.

Regarding the methods described with respect to FIGS. 8 and 9, when a window controller is integrated into a building network or a BMS, outputs from sensors may be input to a network of BMS and provided as input to the window controller. For example, in some embodiments, output signals from any two or more sensors are received. In some embodiments, only one output signal is received, and in some other embodiments, three, four, five, or more outputs are received. These output signals may be received over a building network or a BMS.

A level of tint for the tintable window is determined using a relationship between the received output signals and the level of tint. In some embodiments, determining the level of tint includes using scheduling information for the building. For example, in some embodiments, the scheduling information includes time of year and/or time of day information for the building. In some embodiments, the scheduling information further includes information about the geographical facing direction of the tintable window and the latitude of the building. The lookup table used to determine the level of tint of the windows or the weighting constants used in a relationship used to determine the level of tint of the windows may change according to the schedule.

The window controllers and the methods of controlling the tint state of a tintable window described herein may employ different sensors or combinations of sensors. Different sensors or combinations of sensors may be referred to as different "sensor setups" or "levels." For example, use of an exterior photosensor may be referred to as "level 0," use of an exterior photosensor and an interior photosensor may be referred to as "level 1," use of an exterior photosensor, an interior photosensor, and an occupancy sensor may be referred to as "level 2," and use of an exterior photosensor, an interior photosensor, an occupancy sensor, and a signal indicating energy or power consumption by a heating system, a cooling system, and/or lighting within the building (described below) may be referred to as "level 3." Embodiments of each of these different levels are described further, below.

In some embodiments, the output signals include a signal from an exterior photosensor (i.e., level 0). The relationship employed to determine the level of tint may include an expression or look up table in which the level of tint is the dependent variable and the signal from the exterior photosensor is the independent variable. In some embodiments, the relationship employed in operation 810 uses scheduling information including time of year and/or time of day information for the building. For example, a different relationship over a 24 hour day may be used for each calendar day of the year.

In some embodiments, the output signals include a signal from an exterior photosensor and a signal from an interior photosensor (i.e., level 1). The relationship employed to determine the level of tint may include an expression or look up table in which the level of tint is the dependent variable and the signals from the exterior photosensor and the interior photosensor are independent variables. In some embodiments, the relationship employed in operation 810 uses scheduling information including time of year and/or time of day information for the building. For example, a different relationship over a 24 hour day may be used for each calendar day of the year.

In some embodiments, the output signals received include a signal from an exterior photosensor, a signal from an interior photosensor, and a signal from an occupancy sensor (i.e., level 2). The relationship employed to determine the level of tint may include an expression or look up table in which the level of tint is the dependent variable and the signals from the exterior photosensor, the interior photosensor, and the occupancy sensor are independent variables. In some embodiments, when the occupancy sensor indicates that the room is not occupied, the room may enter into a maximum energy savings mode.

In some embodiments, the output signals received include a signal indicating energy or power consumption by a heating system, a cooling system, and/or lighting within the building. For example, the energy or power consumption of the heating system, the cooling system, and/or the lighting of the building may be monitored to provide the signal indicating energy or power consumption. Devices may be interfaced with or attached to the circuits and/or wiring of the building to enable this monitoring. Alternatively, the power systems in the building may be installed such that the power consumed by the heating system, a cooling system, and/or lighting for an individual room within the building or a group of rooms within the building can be monitored.

For example, with respect to lighting in the building, a signal indicating the energy or power consumption of a light, group of lights, or a lighting system within the building is received. The light, the group of lights, or the lighting system may include at least one light within about 20 feet or about 30 feet of a tintable window, in an area where changing the tint of the window can influence the lighting in the area.

As another example, with respect to the heating and/or cooling in the building, a signal indicating the energy or power consumption of a heating or cooling device providing temperature control within the building is received. The heating or cooling device may be heating or cooling an area of the building within about 50 feet of a tintable window.

In some embodiments, the output signals received include a signal from an exterior photosensor, a signal from an interior photosensor, a signal from an occupancy sensor, and an energy or power consumption signal (i.e., level 3). The energy or power consumption signal indicates energy or power consumption by a heating system, a cooling system, and/or lighting in the building or by room in the building. The relationship employed to determine the level of tint reduces energy consumption by a heating system, a cooling system, and/or lighting in the building while providing conditions suitable for occupancy of the building.

Instructions are then provided to change the tint of the tintable window to the determined level of tint. For example, referring to FIG. 11, this may include master network controller 1103 issuing commands to one or more intermediate network controllers 1105a and 1105b, which in turn issue commands to end controllers 1110 that control each window of the building. End controllers 1100 may apply voltage and/or current to the window to drive the change in tint pursuant to the instructions.

In some embodiments, a building including electrochromic windows and a BMS may be enrolled in or participate in a program run by the utility or utilities providing power to the building. The program may be a program in which the energy consumption of the building is reduced when a peak load occurrence is expected. The utility may send out a warning signal prior to an expected peak load occurrence. For example, the warning may be sent on the day before, the morning of, or about one hour before the expected peak load occurrence. A peak load occurrence may be expected to occur on a hot summer day when cooling systems/air conditioners are drawing a large amount of power from the utility, for example. The warning signal may be received by the BMS of the building or by window controllers configured to control the electrochromic windows in the building. The BMS can then instruct the window controller(s) to transition the appropriate electrochromic windows to a colored state to aid in reducing the power draw of the cooling systems in the building at the time when the peak load is expected.

In some embodiments, tintable windows for the exterior windows of the building (i.e., windows separating the interior of the building from the exterior of the building), may be grouped in zones, with tintable windows in a zone being instructed in a similar manner. For example, groups of electrochromic windows on different floors of the building or different sides of the building may be in different zones. For example, on the first floor of the building, all of the east facing electrochromic windows may be in zone 1, all of the south facing electrochromic windows may be in zone 2, all of the west facing electrochromic windows may be in zone 3, and all of the north facing electrochromic windows may be in zone 4. As another example, all of the electrochromic windows on the first floor of the building may be in zone 1, all of the electrochromic windows on the second floor may be in zone 2, and all of the electrochromic windows on the third floor may be in zone 3. As yet another example, all of the east facing electrochromic windows may be in zone 1, all of the south facing electrochromic windows may be in zone 2, all of the west facing electrochromic windows may be in zone 3, and all of the north facing electrochromic windows may be in zone 4. As yet another example, east facing electrochromic windows on one floor could be divided into different zones. Any number of tintable windows on the same side and/or different sides and/or different floors of the building may be assigned to a zone.

In some embodiments, electrochromic windows in a zone may be controlled by the same window controller. In some other embodiments, electrochromic windows in a zone may be controlled by different window controllers, but the window controllers may all receive the same output signals from sensors and use the same function or lookup table to determine the level of tint for the windows in a zone.

In some embodiments, electrochromic windows in a zone may be controlled by a window controller or controllers that receive an output signal from a transmissivity sensor. In some embodiments, the transmissivity sensor may be mounted proximate the windows in a zone. For example, the transmissivity sensor may be mounted in or on a frame containing an IGU (e.g., mounted in or on a mullion, the horizontal sash of a frame) included in the zone. In some other embodiments, electrochromic windows in a zone that includes the windows on a single side of the building may be controlled by a window controller or controllers that receive an output signal from a transmissivity sensor.

In some embodiments, a transmissivity sensor may provide an output signal to a window controller to control the electrochromic windows of a first zone (e.g., a master control zone). The window controller may also control the electrochromic windows in a second zone (e.g., a slave control zone) in the same manner as the first zone. In some other embodiments, another window controller may control the electrochromic windows in the second zone in the same manner as the first zone.

In some embodiments, a building manager, occupants of rooms in the second zone, or other person may manually instruct (using a tint or clear command or a command from a user console of a BMS, for example) the electrochromic windows in the second zone (i.e., the slave control zone) to enter a tint state or a clear state. In some embodiments, when the tint state of the windows in the second zone is overridden with such a manual command, the electrochromic windows in the first zone (i.e., the master control zone) remain under control of the window controller receiving output from the transmissivity sensor. The second zone may remain in a manual command mode for a period of time and then revert back to be under control of the window controller receiving output from the transmissivity sensor. For example, the second zone may stay in a manual mode for one hour after receiving an override command, and then may revert back to be under control of the window controller receiving output from the transmissivity sensor.

In some embodiments, a building manager, occupants of rooms in the first zone, or other person may manually instruct (using a tint command or a command from a user console of a BMS, for example) the electrochromic windows in the first zone (i.e., the master control zone) to enter a tint state or a clear state. In some embodiments, when the tint state of the windows in the first zone is overridden with such a manual command, the electrochromic windows in the second zone (i.e., the slave control zone) remain under control of the window controller receiving outputs from the exterior photosensor. The first zone may remain in a manual command mode for a period of time and then revert back to be under control of window controller receiving output from the transmissivity sensor. For example, the first zone may stay in a manual mode for one hour after receiving an override command, and then may revert back to be under control of the window controller receiving output from the transmissivity sensor. In some other embodiments, the electrochromic windows in the second zone may remain in the tint state that they are in when the manual override for the first zone is received. The first zone may remain in a manual command mode for a period of time and then both the first zone and the second zone may revert back to be under control of the window controller receiving output from the transmissivity sensor.

Any of the methods described herein of control of a tintable window, regardless of whether the window controller is a standalone window controller or is interfaced with a building network, may be used control the tint of a tintable window.

Wireless or Wired Communication

In some embodiments, window controllers described herein include components for wired or wireless communication between the window controller, sensors, and separate communication nodes. Wireless or wired communications may be accomplished with a communication interface that interfaces directly with the window controller. Such interface could be native to the microprocessor or provided via additional circuitry enabling these functions.

A separate communication node for wireless communications can be, for example, another wireless window controller, an end, intermediate, or master window controller, a remote control device, or a BMS. Wireless communication is used in the window controller for at least one of the following operations: programming and/or operating the EC window, collecting data from the EC window from the various sensors and protocols described herein, and using the EC window as a relay point for wireless communication. Data collected from EC windows also may include count data such as number of times an EC device has been activated, efficiency of the EC device over time, and the like. These wireless communication features is described in more detail below.

In one embodiment, wireless communication is used to operate the associated electrochromic windows, for example, via an infrared (IR), and/or radio frequency (RF) signal. In certain embodiments, the controller will include a wireless protocol chip, such as Bluetooth, EnOcean, WiFi, Zigbee, and the like. Window controllers may also have wireless communication via a network. Input to the window controller can be manually input by a user, either directly or via wireless communication, or the input can be from a BMS of a building of which the electrochromic window is a component.

In one embodiment, when the window controller is part of a distributed network of controllers, wireless communication is used to transfer data to and from each of a plurality of electrochromic windows via the distributed network of controllers, each having wireless communication components. For example, referring again to FIG. 11, master network controller 1103, communicates wirelessly with each of intermediate network controllers 1105a and 1105b, which in turn communicate wirelessly with end controllers 1110, each associated with an electrochromic window. Master network controller 1103 may also communicate wirelessly with the BMS. In one embodiment, at least one level of communication in the window controller is performed wirelessly.

In some embodiments, more than one mode of wireless communication is used in the window controller distributed network. For example, a master window controller may communicate wirelessly to intermediate controllers via WiFi or Zigbee, while the intermediate controllers communicate with end controllers via Bluetooth, Zigbee, EnOcean, or other protocol. In another example, window controllers have redundant wireless communication systems for flexibility in end user choices for wireless communication.

Wireless communication between, for example, master and/or intermediate window controllers and end window controllers offers the advantage of obviating the installation of hard communication lines. This is also true for wireless communication between window controllers and BMS. In one aspect, wireless communication in these roles is useful for data transfer to and from electrochromic windows for operating the window and providing data to, for example, a BMS for optimizing the environment and energy savings in a building. Window location data as well as feedback from sensors are synergized for such optimization. For example, granular level (window-by-window) microclimate information is fed to a BMS in order to optimize the building's various environments.

Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the appended claims.

We claim:

1. An energy management system, the system comprising:
   (a) a Building Management System (BMS);
   (b) one or more windows capable of undergoing reversible optical transitions, wherein at least one of the windows comprises a first conductive layer, a second conductive layer, and an electrochromic layer between the first conductive layer and the second conductive layer;
   (c) a window controller for controlling the one or more windows, the window controller comprising:
      (i) at least one input for receiving data,
      (ii) at least one output for transmitting data, and
      (iii) one or more processors configured to control functions comprising:
         measuring transmittance of at least one of the one or more windows,
         powering a reversible optical transition between at least a bleached end state and a colored end state of the at least one of the one or more windows, wherein powering is based on the measured transmittance of the at least one window, wherein powering the reversible optical transition comprises applying a DC voltage to the first conductive layer and to the second conductive layer to provide an electrical potential across the electrochromic layer establishing a load, wherein the load is floated, and
         communicating with a separate communication node; and
   (d) a network over which the window controller, the BMS, and the one or more windows capable of undergoing reversible optical transitions can communicate.

2. The energy management system of claim 1, wherein the at least one input is configured to receive data from the BMS.

3. The energy management system of claim 1, wherein the at least one output is configured to transmit data to the BMS.

4. The energy management system of claim 1, wherein the at least one input is configured to receive data from the BMS and the at least one output is configured to transmit data to the BMS.

5. The energy management system of claim 1, further comprising (e) at least one sensor, wherein the at least one input is configured to receive data from the at least one sensor.

6. The energy management system of claim 5, wherein the at least one sensor includes one or more photosensors on a roof of a building having the one or more windows, and wherein powering is also based on irradiance/illumination measured by the one or more photosensors.

7. The energy management system of claim 1, wherein the at least one input is configured to receive data from a sensor proximate the at least one of the one or more windows.

8. The energy management system of claim 1, wherein the one or more windows are in a zone, wherein the at least one input is configured to receive data from a sensor proximate one of the windows in the zone.

9. The energy management system of claim 1, wherein the at least one input is configured to receive data from a transmissivity sensor configured to measure transmittance of the at least one window.

10. The energy management system of claim 1, wherein the BMS further comprises a user console for receiving instructions, wherein the at least one input is configured to receive instructions from the user console.

* * * * *